(12) United States Patent
Ludwig et al.

(10) Patent No.: US 7,838,210 B2
(45) Date of Patent: *Nov. 23, 2010

(54) SPERM SUSPENSIONS FOR SORTING INTO X OR Y CHROMOSOME-BEARING ENRICHED POPULATIONS

(75) Inventors: Cindy L. Ludwig, St. Louis, MO (US); Kathleen S. Crowley, Webster Groves, MO (US); Charles N. Graves, Urbana, IL (US)

(73) Assignee: Inguran, LLC., Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/092,313

(22) Filed: Mar. 29, 2005

(65) Prior Publication Data

US 2005/0244805 A1    Nov. 3, 2005

Related U.S. Application Data

(60) Provisional application No. 60/618,440, filed on Oct. 13, 2004, provisional application No. 60/614,178, filed on Sep. 29, 2004, provisional application No. 60/557,407, filed on Mar. 29, 2004.

(51) Int. Cl.
    *A01N 1/02* (2006.01)
(52) U.S. Cl. .................... 435/2; 435/287.1; 435/6; 435/93.7
(58) Field of Classification Search ............... 435/40.5, 435/325, 2
    See application file for complete search history.

(56) References Cited

U.S. PATENT DOCUMENTS

| | | | |
|---|---|---|---|
| 3,005,756 A | 10/1961 | Van Demark et al. |
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,251,733 A | 2/1981 | Hirlman, Jr. |
| 4,255,021 A | 3/1981 | Brunsden |

(Continued)

FOREIGN PATENT DOCUMENTS

BR    9704313    6/1999

(Continued)

OTHER PUBLICATIONS

Baumber, J., et al., "The Effect of Reactive Oxygen Species on Equine Sperm Motility, Viability, Acrosomal Integrity, Mitochondrial Membrane Potential, and Membrane Lipid Peroxidation," J of Andrology, 2000, vol. 21(6), pp. 895-902.

(Continued)

*Primary Examiner*—Ralph Gitomer
*Assistant Examiner*—Tiffany M Gough

(57) ABSTRACT

Sperm cell suspensions comprising a motility inhibitor are disclosed. The cells contained in such suspensions tend to have a greater capacity for enduring the various process steps typically associated with the sorting of sperm cells into gender enriched populations, thereby resulting in post-sort compositions with an increased number of viable or motile sperm. Processes for forming such cell suspensions, as well as processes for staining sperm cells, are also disclosed.

20 Claims, 20 Drawing Sheets

U.S. PATENT DOCUMENTS

| | | |
|---|---|---|
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Toboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junnila |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |

| | | | | | |
|---|---|---|---|---|---|
| 5,259,593 A | 11/1993 | Orme et al. | 5,665,315 A | 9/1997 | Robert et al. |
| 5,260,764 A | 11/1993 | Fukuda et al. | 5,672,880 A | 9/1997 | Kain |
| 5,274,240 A | 12/1993 | Mathies et al. | 5,674,743 A | 10/1997 | Ulmer |
| 5,275,787 A | 1/1994 | Yuguchi et al. | 5,675,401 A | 10/1997 | Wangler et al. |
| 5,298,967 A | 3/1994 | Wells | 5,682,038 A | 10/1997 | Hoffman |
| 5,315,122 A | 5/1994 | Pinsky et al. | 5,684,575 A | 11/1997 | Steen |
| 5,316,540 A | 5/1994 | McMannis et al. | 5,687,727 A | 11/1997 | Kraus et al. |
| 5,317,162 A | 5/1994 | Pinsky et al. | 5,690,815 A | 11/1997 | Krasnoff et al. |
| 5,346,990 A | 9/1994 | Spaulding | 5,690,895 A | 11/1997 | Matsumoto et al. |
| RE34,782 E | 11/1994 | Dandliker et al. | 5,691,133 A | 11/1997 | Critser et al. |
| 5,359,907 A | 11/1994 | Baker et al. | 5,693,534 A | 12/1997 | Alak et al. |
| 5,366,888 A | 11/1994 | Fry et al. | 5,696,157 A | 12/1997 | Wang et al. |
| 5,367,474 A | 11/1994 | Auer et al. | 5,699,152 A | 12/1997 | Fedor et al. |
| 5,370,842 A | 12/1994 | Miyazaki et al. | 5,700,692 A | 12/1997 | Sweet |
| 5,371,585 A | 12/1994 | Morgan et al. | 5,701,012 A | 12/1997 | Ho |
| 5,395,588 A | 3/1995 | North, Jr. et al. | 5,707,808 A | 1/1998 | Roslaniec et al. |
| 5,400,179 A | 3/1995 | Ito | 5,708,868 A | 1/1998 | Ishikawa |
| 5,412,466 A | 5/1995 | Ogino | 5,712,807 A | 1/1998 | Bangham |
| 5,437,987 A | 8/1995 | Ten et al. | 5,719,666 A | 2/1998 | Fukuda et al. |
| 5,439,362 A | 8/1995 | Spaulding | 5,719,667 A | 2/1998 | Miers |
| 5,444,527 A | 8/1995 | Kosaka | 5,726,009 A | 3/1998 | Connors et al. |
| 5,447,841 A | 9/1995 | Grey et al. | 5,726,364 A | 3/1998 | Van den Engh |
| 5,447,842 A | 9/1995 | Simons | 5,726,751 A | 3/1998 | Altendorf et al. |
| 5,452,054 A | 9/1995 | Dewa et al. | 5,730,941 A | 3/1998 | Lefevre et al. |
| 5,457,526 A | 10/1995 | Kosaka | 5,736,330 A | 4/1998 | Fulton |
| 5,461,145 A | 10/1995 | Kudo et al. | 5,739,902 A | 4/1998 | Gjelsnes et al. |
| 5,464,581 A | 11/1995 | Van den Engh | 5,745,308 A | 4/1998 | Spangenberg |
| 5,466,572 A | 11/1995 | Sasaki et al. | 5,747,349 A | 5/1998 | den Engh et al. |
| 5,467,189 A | 11/1995 | Kreikebaum et al. | 5,759,767 A | 6/1998 | Lakowicz et al. |
| 5,469,375 A | 11/1995 | Kosaka | 5,777,732 A | 7/1998 | Hanninen et al. |
| 5,471,294 A | 11/1995 | Ogino | 5,780,230 A | 7/1998 | Li et al. |
| 5,471,299 A | 11/1995 | Kaye et al. | 5,786,560 A | 7/1998 | Tatah et al. |
| 5,475,487 A | 12/1995 | Mariella, Jr. et al. | 5,790,692 A | 8/1998 | Price et al. |
| 5,480,774 A | 1/1996 | Hew et al. | 5,793,485 A | 8/1998 | Gourley |
| 5,480,775 A | 1/1996 | Ito et al. | 5,796,112 A | 8/1998 | Ichie |
| 5,483,469 A | 1/1996 | Van den Engh et al. | 5,798,276 A | 8/1998 | Haugland et al. |
| 5,488,469 A | 1/1996 | Yamamoto et al. | 5,799,830 A | 9/1998 | Carroll et al. |
| 5,492,534 A | 2/1996 | Atheyde | 5,804,436 A | 9/1998 | Okun et al. |
| 5,494,795 A | 2/1996 | Guerry et al. | 5,815,262 A | 9/1998 | Schrof et al. |
| 5,495,719 A | 3/1996 | Gray, Jr. | 5,819,948 A | 10/1998 | Van den Engh |
| 5,496,272 A | 3/1996 | Chung et al. | 5,824,269 A | 10/1998 | Kosaka et al. |
| 5,503,994 A | 4/1996 | Shear et al. | 5,831,723 A | 11/1998 | Kubota et al. |
| 5,514,537 A | 5/1996 | Chandler | 5,835,262 A | 11/1998 | Iketaki et al. |
| 5,523,573 A | 6/1996 | Hanninen et al. | 5,840,504 A | 11/1998 | Blecher |
| 5,532,155 A | 7/1996 | Ranoux | 5,844,685 A | 12/1998 | Gontin |
| 5,547,849 A | 8/1996 | Baer et al. | 5,846,737 A | 12/1998 | Kang |
| 5,548,395 A | 8/1996 | Kosaka | 5,866,344 A | 2/1999 | Georgiou |
| 5,548,661 A | 8/1996 | Price et al. | 5,868,767 A | 2/1999 | Farley et al. |
| 5,550,058 A | 8/1996 | Corio et al. | 5,872,627 A | 2/1999 | Miers |
| 5,556,764 A | 9/1996 | Sizto et al. | 5,873,254 A | 2/1999 | Arav |
| 5,558,998 A | 9/1996 | Hammond et al. | 5,874,266 A | 2/1999 | Paisson |
| 5,559,032 A | 9/1996 | Pomeroy et al. | 5,876,942 A | 3/1999 | Cheng et al. |
| 5,578,449 A | 11/1996 | Frasch et al. | 5,880,457 A | 3/1999 | Tomiyama et al. |
| 5,579,159 A | 11/1996 | Ito | 5,880,474 A | 3/1999 | Norton et al. |
| 5,584,982 A | 12/1996 | Dovichi et al. | 5,883,378 A | 3/1999 | Irish et al. |
| 5,589,457 A | 12/1996 | Wiltbank | 5,888,730 A | 3/1999 | Gray et al. |
| 5,596,401 A | 1/1997 | Kusuzawa | 5,891,734 A | 4/1999 | Gill et al. |
| 5,601,234 A | 2/1997 | Larue | 5,893,843 A | 4/1999 | Rodrigues |
| 5,601,235 A | 2/1997 | Booker et al. | 5,895,764 A | 4/1999 | Sklar et al. |
| 5,601,533 A | 2/1997 | Hancke et al. | 5,895,922 A | 4/1999 | Ho |
| 5,602,039 A | 2/1997 | Van den Engh | 6,704,313 B1 | 4/1999 | De Resende et al. |
| 5,602,349 A | 2/1997 | Van den Engh | 5,899,848 A | 5/1999 | Haubrich |
| 5,608,519 A | 3/1997 | Grouley et al. | 5,909,278 A | 6/1999 | Deka et al. |
| 5,620,842 A | 4/1997 | Davis et al. | 5,912,257 A | 6/1999 | Prasad et al. |
| 5,622,820 A | 4/1997 | Rossi | 5,916,144 A | 6/1999 | Prather et al. |
| 5,627,037 A | 5/1997 | Ward et al. | 5,916,449 A | 6/1999 | Ellwart et al. |
| 5,633,503 A | 5/1997 | Kosaka | 5,917,733 A | 6/1999 | Bangham |
| 5,641,457 A | 6/1997 | Vardanega | 5,919,360 A | 7/1999 | Contaxis, III et al. |
| 5,643,796 A | 7/1997 | Van Den Engh et al. | 5,919,621 A | 7/1999 | Brown |
| 5,650,847 A | 7/1997 | Maltsev et al. | 5,934,885 A | 8/1999 | Farrell et al. |
| 5,658,751 A | 8/1997 | Yue et al. | 5,962,238 A | 10/1999 | Sizto et al. |
| 5,660,997 A | 8/1997 | Spaulding | 5,972,710 A | 10/1999 | Weigl et al. |
| 5,663,048 A | 9/1997 | Winkfein et al. | 5,973,842 A | 10/1999 | Spangenberg |

| | | | | | |
|---|---|---|---|---|---|
| 5,985,216 A | 11/1999 | Rens et al. | 6,432,638 B2 | 8/2002 | Dervan et al. |
| 5,985,538 A | 11/1999 | Stachecki | 6,452,372 B1 | 9/2002 | Husher et al. |
| 5,990,479 A | 11/1999 | Weiss et al. | 6,454,945 B1 | 9/2002 | Weigl et al. |
| 5,991,028 A | 11/1999 | Cabib et al. | 6,456,055 B2 | 9/2002 | Shinabe et al. |
| 5,998,140 A | 12/1999 | Dervan et al. | 6,463,314 B1 | 10/2002 | Haruna |
| 5,998,212 A | 12/1999 | Corio et al. | 6,465,169 B2 | 10/2002 | Walderich et al. |
| 6,002,471 A | 12/1999 | Quake | 6,473,176 B2 | 10/2002 | Basiji et al. |
| 6,003,678 A | 12/1999 | Van den Engh | 6,482,652 B2 | 11/2002 | Furlong et al. |
| 6,042,025 A | 3/2000 | Crampton et al. | 6,489,092 B1 | 12/2002 | Benjamin et al. |
| 6,042,249 A | 3/2000 | Spangenberg | 6,495,333 B1 | 12/2002 | Willmann et al. |
| 6,050,935 A | 4/2000 | Ranoux et al. | 6,495,366 B1 | 12/2002 | Briggs |
| 6,071,689 A | 6/2000 | Seidel et al. | 6,503,698 B1 | 1/2003 | Dobrinsky et al. |
| 6,079,836 A | 6/2000 | Burr et al. | 6,511,853 B1 | 1/2003 | Kopf-Sill et al. |
| 6,086,574 A | 7/2000 | Carroll et al. | 6,514,722 B2 | 2/2003 | Paisson et al. |
| 6,087,352 A | 7/2000 | Trout | 6,524,860 B1 | 2/2003 | Seidel et al. |
| 6,090,947 A | 7/2000 | Dervan et al. | 6,528,802 B1 | 3/2003 | Koenig et al. |
| 6,097,485 A | 8/2000 | Lievan | 6,534,308 B1 | 3/2003 | Palsson et al. |
| 6,111,398 A | 8/2000 | Graham | 6,537,829 B1 | 3/2003 | Zarling et al. |
| 6,117,068 A | 9/2000 | Gourley et al. | 6,540,895 B1 | 4/2003 | Spence et al. |
| 6,119,465 A | 9/2000 | Mullens et al. | 6,563,583 B2 | 5/2003 | Ortyn et al. |
| 6,120,735 A | 9/2000 | Zborowski et al. | 6,569,464 B1 | 5/2003 | Mukherjee et al. |
| 6,128,133 A | 10/2000 | Bergmann | 6,576,291 B2 | 6/2003 | Bawendi et al. |
| 6,130,034 A | 10/2000 | Aitken | 6,577,387 B2 | 6/2003 | Ross, III et al. |
| 6,132,961 A | 10/2000 | Gray et al. | 6,580,504 B1 | 6/2003 | Ortyn et al. |
| 6,133,044 A | 10/2000 | Van den Engh | 6,587,203 B2 | 7/2003 | Colon |
| 6,133,995 A | 10/2000 | Kubota | 6,589,792 B1 | 7/2003 | Malachowski |
| 6,139,800 A | 10/2000 | Chandler | 6,590,911 B1 | 7/2003 | Spinelli et al. |
| 6,140,121 A | 10/2000 | Ellington et al. | 6,596,143 B1 | 7/2003 | Wang et al. |
| 6,143,535 A | 11/2000 | Paisson | 6,596,499 B2 | 7/2003 | Jalink |
| 6,143,901 A | 11/2000 | Dervan | 6,604,435 B2 | 8/2003 | Buchanan et al. |
| 6,146,837 A | 11/2000 | van de Winkel | 6,613,525 B2 | 9/2003 | Nelson et al. |
| 6,149,867 A | 11/2000 | Seidel et al. | 6,617,107 B1 | 9/2003 | Dean |
| 6,153,373 A | 11/2000 | Benjamin et al. | 6,618,143 B2 | 9/2003 | Roche et al. |
| 6,154,276 A | 11/2000 | Mariella, Jr. | 6,618,679 B2 | 9/2003 | Loehrlein et al. |
| 6,175,409 B1 | 1/2001 | Nielsen et al. | 6,641,708 B1 | 11/2003 | Becker et al. |
| 6,177,277 B1 | 1/2001 | Soini | 6,642,018 B1 | 11/2003 | Koller et al. |
| 6,193,647 B1 | 2/2001 | Beebe et al. | 6,658,357 B2 | 12/2003 | Chandler |
| 6,201,628 B1 | 3/2001 | Basiji et al. | 6,664,550 B2 | 12/2003 | Rader et al. |
| 6,207,392 B1 | 3/2001 | Weiss et al. | 6,667,830 B1 | 12/2003 | Iketaki et al. |
| 6,208,411 B1 | 3/2001 | Vaez-Iravani | 6,671,044 B2 | 12/2003 | Ortyn et al. |
| 6,211,477 B1 | 4/2001 | Cardott et al. | 6,673,095 B2 | 1/2004 | Nordquist |
| 6,214,560 B1 | 4/2001 | Yguerabide et al. | 6,674,525 B2 | 1/2004 | Bardell et al. |
| 6,221,654 B1 | 4/2001 | Quake et al. | 6,698,627 B2 | 3/2004 | Garcia et al. |
| 6,221,671 B1 | 4/2001 | Groner et al. | 6,700,130 B2 | 3/2004 | Fritz |
| 6,238,920 B1 | 5/2001 | Nagai et al. | 6,703,621 B2 | 3/2004 | Wolleschensky |
| 6,247,323 B1 | 6/2001 | Maeda | 6,706,163 B2 | 3/2004 | Seul et al. |
| 6,248,590 B1 | 6/2001 | Malachowski | 6,707,555 B1 | 3/2004 | Kusuzawa et al. |
| 6,256,096 B1 | 7/2001 | Johnson | 6,713,019 B2 | 3/2004 | Ozasa et al. |
| 6,263,745 B1 | 7/2001 | Buchanan et al. | 6,729,369 B2 | 5/2004 | Neas et al. |
| 6,283,920 B1 | 9/2001 | Eberle et al. | 6,746,873 B1 | 6/2004 | Buchanan et al. |
| 6,296,810 B1 | 10/2001 | Ulmer | 6,752,298 B2 | 6/2004 | Garcia et al. |
| 6,309,815 B1 | 10/2001 | Tash et al. | 6,753,161 B2 | 6/2004 | Koller et al. |
| 6,316,234 B1 | 11/2001 | Bova | 6,761,286 B2 | 7/2004 | Py et al. |
| 6,317,511 B1 | 11/2001 | Horiuchi | 6,761,288 B2 | 7/2004 | Garcia |
| 6,322,901 B1 | 11/2001 | Bawendi et al. | 6,767,706 B2 | 7/2004 | Quake |
| 6,323,632 B1 | 11/2001 | Husher et al. | 6,780,377 B2 | 8/2004 | Hall et al. |
| 6,326,144 B1 | 12/2001 | Bawendi et al. | 6,782,768 B2 | 8/2004 | Buchanan et al. |
| 6,328,071 B1 | 12/2001 | Austin | 6,789,706 B2 | 9/2004 | Abergel et al. |
| 6,329,158 B1 | 12/2001 | Hoffman et al. | 6,789,750 B1 | 9/2004 | Heldt |
| 6,332,540 B1 | 12/2001 | Paul et al. | 6,793,387 B1 | 9/2004 | Neas et al. |
| 6,357,307 B2 | 3/2002 | Buchanan et al. | 6,813,017 B1 | 11/2004 | Hoffman et al. |
| 6,368,786 B1 | 4/2002 | Saint-Ramon et al. | 6,819,411 B1 | 11/2004 | Sharpe et al. |
| 6,372,422 B1 | 4/2002 | Seidel et al. | 6,849,394 B2 | 2/2005 | Rozeboom et al. |
| 6,372,506 B1 | 4/2002 | Norton | 6,849,423 B2 | 2/2005 | Mutz et al. |
| 6,384,951 B1 | 5/2002 | Basiji et al. | 6,861,265 B1 | 3/2005 | Van den Engh |
| 6,395,305 B1 | 5/2002 | Buhr et al. | 6,941,005 B2 | 9/2005 | Lary et al. |
| 6,400,453 B1 | 6/2002 | Hansen | 7,015,310 B2 | 3/2006 | Remington |
| 6,411,835 B1 | 6/2002 | Modell et al. | 7,094,527 B2 | 8/2006 | Seidel et al. |
| 6,411,904 B1 | 6/2002 | Chandler | 7,105,355 B2 | 9/2006 | Kurabayashi et al. |
| 6,416,190 B1 | 7/2002 | Grier et al. | 7,195,920 B2 | 3/2007 | Seidel et al. |
| 6,423,505 B1 | 7/2002 | Davis | 7,208,265 B1 | 4/2007 | Schenk |
| 6,423,551 B1 | 7/2002 | Weiss et al. | 7,221,453 B2 | 5/2007 | Sharpe et al. |
| 6,432,630 B1 | 8/2002 | Blankenstein | 7,335,507 B2 | 2/2008 | Anzar et al. |

| | | | | | | |
|---|---|---|---|---|---|---|
| 2001/0006416 A1 | 7/2001 | Johnson | | EP | 0 026 770 B1 | 3/1983 |
| 2002/0047697 A1 | 4/2002 | Husher et al. | | EP | 0 029 662 B1 | 2/1984 |
| 2002/0058332 A1 | 5/2002 | Quake et al. | | EP | 0 025 296 B1 | 5/1985 |
| 2002/0064809 A1 | 5/2002 | Mutz et al. | | EP | 0140616 | 5/1985 |
| 2002/0096123 A1 | 7/2002 | Whittier et al. | | EP | 0 158 147 A2 | 10/1985 |
| 2002/0115055 A1 | 8/2002 | Matta | | EP | 0 160 201 A2 | 11/1985 |
| 2002/0119558 A1 | 8/2002 | Seidel et al. | | EP | 0 229 814 B1 | 7/1987 |
| 2002/0131957 A1 | 9/2002 | Gavin | | EP | 0 246 604 A2 | 11/1987 |
| 2002/0171827 A1 | 11/2002 | Van den Engh | | EP | 0288029 B1 | 4/1988 |
| 2002/0182590 A1 | 12/2002 | Strange et al. | | EP | 0276166 A2 | 7/1988 |
| 2002/0186375 A1 | 12/2002 | Asbury et al. | | EP | 0 289 677 A2 | 11/1988 |
| 2002/0186874 A1 | 12/2002 | Price et al. | | EP | 0 316 173 A1 | 5/1989 |
| 2002/0198928 A1 | 12/2002 | Bukshpan et al. | | EP | 0 317 809 A2 | 5/1989 |
| 2003/0048433 A1 | 3/2003 | Desjonqueres | | EP | A-0 366794 | 5/1990 |
| 2003/0059764 A1 | 3/2003 | Ravkin et al. | | EP | 0 409 293 A2 | 1/1991 |
| 2003/0059945 A1 | 3/2003 | Dzekunov et al. | | EP | 0 461 618 | 12/1991 |
| 2003/0078703 A1 | 4/2003 | Potts | | EP | 0 463 562 A1 | 1/1992 |
| 2003/0096405 A1 | 5/2003 | Takayama et al. | | EP | 0468100 A1 | 1/1992 |
| 2003/0098421 A1 | 5/2003 | Ho | | EP | 0474 187 A2 | 3/1992 |
| 2003/0113765 A1 | 6/2003 | Dempcy et al. | | EP | 0 316 172 B1 | 7/1992 |
| 2003/0119050 A1 | 6/2003 | Shai | | EP | 0 316 171 B1 | 9/1992 |
| 2003/0119206 A1 | 6/2003 | Shai | | EP | 0570102 A1 | 3/1993 |
| 2003/0129091 A1 | 7/2003 | Seidel et al. | | EP | 0538786 A | 4/1993 |
| 2003/0157475 A1 | 8/2003 | Schenk | | EP | 0 279 000 B1 | 7/1993 |
| 2003/0165812 A1 | 9/2003 | Takayama et al. | | EP | 0 553 951 A1 | 8/1993 |
| 2003/0175917 A1 | 9/2003 | Cumming | | EP | 0 288 029 B1 | 1/1994 |
| 2003/0175980 A1 | 9/2003 | Hayenga et al. | | EP | 0 381 694 B1 | 6/1994 |
| 2003/0190681 A1 | 10/2003 | Shai | | EP | 0 361 504 B1 | 7/1994 |
| 2003/0207461 A1 | 11/2003 | Bell et al. | | EP | 606847 A2 | 7/1994 |
| 2003/0209059 A1 | 11/2003 | Kawano | | EP | 0 289 200 B2 | 8/1994 |
| 2004/0005582 A1 | 1/2004 | Shipwast | | EP | 0 555 212 B1 | 10/1994 |
| 2004/0031071 A1 | 2/2004 | Morris et al. | | EP | 0 361 503 B1 | 11/1994 |
| 2004/0034879 A1 | 2/2004 | Rothstein et al. | | EP | 0 696 731 A2 | 2/1996 |
| 2004/0049801 A1 | 3/2004 | Seidel | | EP | 0 705 978 A2 | 4/1996 |
| 2004/0053243 A1 | 3/2004 | Evans | | EP | 0 711 991 A1 | 5/1996 |
| 2004/0055030 A1 | 3/2004 | Maxwell et al. | | EP | 0 471 758 B1 | 9/1996 |
| 2004/0061070 A1 | 4/2004 | Hansen | | EP | 0 736 765 A1 | 10/1996 |
| 2004/0061853 A1 | 4/2004 | Blasenheim | | EP | 0 545 284 B1 | 2/1997 |
| 2004/0062685 A1 | 4/2004 | Norton et al. | | EP | 0 360 487 B1 | 7/1997 |
| 2004/0072278 A1 | 4/2004 | Chou et al. | | EP | 0 412 431 B1 | 10/1997 |
| 2004/0107150 A1 | 6/2004 | Neas et al. | | EP | 0 526 131 B1 | 1/1998 |
| 2004/0132001 A1 | 7/2004 | Seidel et al. | | EP | A-0 478155 | 1/1998 |
| 2005/0003472 A1 | 1/2005 | Anzar et al. | | EP | 0 822 404 A3 | 2/1998 |
| 2005/0011582 A1 | 1/2005 | Haug | | EP | 0 822 401 A2 | 4/1998 |
| 2005/0064383 A1 | 3/2005 | Bashkin et al. | | EP | 0 556 748 B1 | 10/1998 |
| 2005/0112541 A1 | 5/2005 | Durack et al. | | EP | 0 430 402 B1 | 1/1999 |
| 2005/0214733 A1 | 9/2005 | Graham | | EP | 0 529 666 B1 | 4/2000 |
| 2005/0244805 A1 | 11/2005 | Ludwig et al. | | EP | 0 994 342 A3 | 4/2000 |
| 2005/0282245 A1 | 12/2005 | Ludwig et al. | | EP | 0 752 133 B1 | 6/2000 |
| 2006/0118167 A1 | 6/2006 | Neas et al. | | EP | 1 018 644 A2 | 7/2000 |
| 2006/0147894 A1 | 7/2006 | Sowter | | EP | 1 118 268 A1 | 7/2001 |
| 2006/0203226 A1 | 9/2006 | Roche et al. | | EP | 1 147 774 A1 | 10/2001 |
| 2006/0263829 A1 | 11/2006 | Evans et al. | | EP | 0 534 033 B1 | 11/2001 |
| 2006/0281176 A1 | 12/2006 | Seidel et al. | | EP | 0 925 494 B1 | 12/2001 |
| 2007/0026378 A1 | 2/2007 | Schenk | | EP | 0 748 316 B1 | 5/2002 |
| 2007/0026379 A1 | 2/2007 | Seidel et al. | | EP | 0 662 124 B1 | 6/2002 |
| 2007/0042342 A1 | 2/2007 | Seidel et al. | | EP | 1 245 944 A3 | 10/2002 |
| 2007/0092860 A1 | 4/2007 | Schenk | | EP | 1 249 502 A2 | 10/2002 |
| 2007/0099171 A1 | 5/2007 | Schenk | | EP | 1250897 A1 | 10/2002 |
| 2007/0099260 A1 | 5/2007 | Seidel et al. | | EP | 1 380 304 A2 | 1/2004 |
| 2007/0117086 A1 | 5/2007 | Evans et al. | | EP | 1 403 633 A3 | 4/2004 |
| 2007/0123461 A1 | 5/2007 | Josephson | | EP | 1 100 400 B1 | 5/2004 |
| 2007/0248976 A1 | 10/2007 | Harding | | EP | 1 257 168 B1 | 2/2005 |
| | | | | GB | 1471019 | 4/1977 |
| | FOREIGN PATENT DOCUMENTS | | | GB | 2 121 976 A | 1/1984 |
| | | | | GB | 2 122 369 A | 1/1984 |
| CA | 1029833 | 4/1978 | | GB | 2 125 181 A | 2/1984 |
| CA | 1 250 808 | 3/1989 | | GB | 2 136 561 A | 9/1984 |
| CA | 2113957 A1 | 1/1994 | | GB | 2 137 352 A | 10/1984 |
| CN | 03109426 | 12/2005 | | GB | 2145112 | 2/1985 |
| EP | 0025296 A2 | 3/1981 | | GB | 2 144 542 A | 3/1985 |
| EP | 0 046 345 A2 | 2/1982 | | GB | 2 153 521 A | 8/1985 |
| EP | 0 068 404 B1 | 1/1983 | | GB | 2 243 681 A | 11/1991 |

| | | |
|---|---|---|
| GB | 2 360 360 A | 9/2001 |
| JP | 61139747 A | 6/1986 |
| JP | 61159135 A | 7/1986 |
| JP | 2024535 | 1/1990 |
| JP | 4126064 A | 4/1992 |
| JP | 4126065 A | 4/1992 |
| JP | 4126066 A | 4/1992 |
| JP | 4126079 A | 4/1992 |
| JP | 4126080 A | 4/1992 |
| JP | 4126081 A | 4/1992 |
| WO | WO 84/01265 A1 | 4/1984 |
| WO | WO 85/04014 A1 | 9/1985 |
| WO | WO 88/07198 | 9/1988 |
| WO | WO 89/04470 A1 | 5/1989 |
| WO | WO 89/04471 A1 | 5/1989 |
| WO | WO 90/13315 A1 | 11/1990 |
| WO | WO 9105236 | 4/1991 |
| WO | WO 92/08120 A1 | 5/1992 |
| WO | WO 92/17288 A1 | 10/1992 |
| WO | WO 93/10803 | 6/1993 |
| WO | WO 9317322 A1 | 9/1993 |
| WO | WO 94/22001 A1 | 9/1994 |
| WO | WO 96/04542 A1 | 2/1996 |
| WO | WO 96/12171 A2 | 4/1996 |
| WO | WO 96/12172 | 4/1996 |
| WO | WO 96/12173 A1 | 4/1996 |
| WO | WO 96/31764 | 10/1996 |
| WO | WO 96/33806 A1 | 10/1996 |
| WO | WO 97/29354 A1 | 8/1997 |
| WO | WO 97/30338 A1 | 8/1997 |
| WO | WO 97/35189 A1 | 9/1997 |
| WO | WO 97/43620 A1 | 11/1997 |
| WO | WO 89/04472 A1 | 5/1998 |
| WO | WO 98/34094 A1 | 8/1998 |
| WO | WO 98/48259 | 10/1998 |
| WO | WO 98/57152 A1 | 12/1998 |
| WO | WO 99/05504 A2 | 2/1999 |
| WO | WO 99/33956 A1 | 7/1999 |
| WO | WO 99/38883 A1 | 8/1999 |
| WO | WO 99/42810 A1 | 8/1999 |
| WO | WO 99/44035 | 9/1999 |
| WO | WO 99/44037 A1 | 9/1999 |
| WO | WO 99/47906 A1 | 9/1999 |
| WO | WO 99/60397 A1 | 11/1999 |
| WO | WO 9957955 | 11/1999 |
| WO | WO 99/61888 A2 | 12/1999 |
| WO | WO 00/06193 A1 | 2/2000 |
| WO | WO 00/12204 | 3/2000 |
| WO | WO 00/36396 | 6/2000 |
| WO | WO 00/49387 | 8/2000 |
| WO | WO 00/54026 | 9/2000 |
| WO | WO 00/56444 | 9/2000 |
| WO | WO 00/70080 | 11/2000 |
| WO | WO 01/02836 A1 | 1/2001 |
| WO | WO 01/28700 A1 | 4/2001 |
| WO | WO 0129538 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/42757 A2 | 6/2001 |
| WO | WO 01/51612 A1 | 7/2001 |
| WO | WO 01/61313 A2 | 8/2001 |
| WO | WO 01/68110 A | 9/2001 |
| WO | WO 01/68226 A2 | 9/2001 |
| WO | WO 01/71348 A1 | 9/2001 |
| WO | WO 01/75161 A2 | 10/2001 |
| WO | WO 0175176 | 10/2001 |
| WO | WO 01/85913 A | 11/2001 |
| WO | WO 01/90295 A1 | 11/2001 |
| WO | WO 01/95815 A1 | 12/2001 |
| WO | WO 02/01189 A1 | 1/2002 |
| WO | WO 02/04666 A2 | 1/2002 |
| WO | WO 02/19594 A | 3/2002 |
| WO | WO 02/19943 A1 | 3/2002 |
| WO | WO 02/20850 A2 | 3/2002 |
| WO | WO 02/21102 A2 | 3/2002 |
| WO | WO 02/23163 A1 | 3/2002 |
| WO | WO 02/25269 A2 | 3/2002 |
| WO | WO 0320877 A2 | 3/2002 |
| WO | WO 02/26114 A2 | 4/2002 |
| WO | WO 02/28311 A1 | 4/2002 |
| WO | WO 02/29106 A2 | 4/2002 |
| WO | WO 02/41906 A2 | 5/2002 |
| WO | WO 0241906 A2 | 5/2002 |
| WO | 0243574 A2 | 6/2002 |
| WO | WO 02/43486 A1 | 6/2002 |
| WO | WO 02/43574 A3 | 6/2002 |
| WO | WO 02/44319 A2 | 6/2002 |
| WO | WO 02/052244 A2 | 7/2002 |
| WO | WO 02/054044 A2 | 7/2002 |
| WO | WO 02/057775 A1 | 7/2002 |
| WO | WO 02/060880 A1 | 8/2002 |
| WO | 02077011 A3 | 10/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | WO 03/056330 A2 | 7/2003 |
| WO | WO 03/056335 A2 | 7/2003 |
| WO | WO 03/072765 A1 | 9/2003 |
| WO | WO 03/078065 A1 | 9/2003 |
| WO | WO 03/078972 A1 | 9/2003 |
| WO | WO 2004001401 | 12/2003 |
| WO | WO 2004/006916 A1 | 1/2004 |
| WO | WO 2004/009237 | 1/2004 |
| WO | WO 2004/009237 A2 | 1/2004 |
| WO | WO 2004/009237 A3 | 1/2004 |
| WO | WO 2004/012837 A2 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/024227 A3 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006/015056 A2 | 2/2006 |
| WO | WO 2006012597 A2 | 2/2006 |
| WO | WO 2006/029653 | 3/2006 |
| WO | WO 2006060770 A2 | 8/2006 |
| WO | WO 2007016090 A2 | 2/2007 |

OTHER PUBLICATIONS

Best, T.P., et al., "Nuclear Localization of Pyrrole-Imidazole Polyamide-Flourescein Conjugates in Cell Culture," PNAS, 2003, vol. 100(21), pp. 12063-12068.

Bruemmer, J.E., et al., "Effect of Pyruvate on the Function of Stallion Spermatozoa Stored for up to 48 Hours," J Anim Sci, 2002, vol. 80, pp. 12-18.

Denniston, D.J., et al., "Effect of Antioxidants on the Motility and Viability of Cooled Stallion Spermatozoa," J Reprod and Fertil, 2001, Supplement 56, pp. 121-126.

Farrell, P.B., et al., "Quantification of Bull Sperm Characteristics Measured by Computer-Assisted Sperm Analysis (CASA) and the Relationship to Fertility," Theriogenology, 1998, vol. 49, pp. 871-879.

Gygi, M.P., et al., "Use of Fluorescent Sequence-Specific Polyamides to Discriminate Human Chromosomes by Microscopy and Flow Cytometry," Nucl Acids Res, 2002, vol. 30(13), pp. 2790-2799.

Johnson, L.A., et al., "Flow Cytometry of X and Y Chromosome-Bearing Sperm for DNA Using an Improved Preparation Method and Staining with Hoechst 33342," Gamete Research, 1987, vol. 17, pp. 203-212.

Salisbury, G.W., et al., "Substrate-Free Epididymal-Like Bovine Spermatozoa," J Reprod Fertil, 1963, vol. 6, pp. 351-359.

Salisbury, G.W., et al., "Preservation of Bovine Spermatozoa in Yolk-Citrate Diluent and Field Results from its Use," J Dairy Sci, 1941, vol. 24(11), pp. 905-910.

Physiology of Reproduction and Artificial Insemination of Cattle, 1978, 2nd Ed., Chap. 16-18, pp. 442-576, Edited by G.W. Salisbury, N. L. VanDemark, J.R. Lodge, published by W.H. Freeman Co., San Francisco, CA.

Garcia, M.A., et al., "Development of a Buffer System for Dialysis of Bovine Spermatozoa Before Freezing. III. Effect of Different Inorganic and Organic Salts on Fresh and Frozen-Thawed Semen," Theriogenology, 1989, vol. 31(5), pp. 1039-1048.

Karow, A.M., et al., "Effects of Temperature, Potassium Concentration, and Sugar on Human Spematozoa Motility: A Cell Preservation Model from Reproductive Medicine," Cryobiology, 1992, vol. 29, pp. 250-254.

Invitation to Pay Additional Fees, Results of Partial International Search, PCT/US2005/010599, dated Sep. 7, 2005.

Schenk, J.L., et al., "Cryopreservation of Flow-Sorted Bovine Spermatozoa," Theriogenology, 1999, 52, pp. 1375-1391.

International Search Report for PCT/US2005/026269 dated Dec. 2, 2005, 7 pages.

Graves, C.N. et al., "Metabolism of Pyruvate by Epididymal-like Bovine Spermatozoa," 1964, J Dairy Sci, vol. 47(12), pp. 1407-1411.

Graves, C.N. et al., "Metabolic End-Products of Anaerobic Spermatozoan Metabolism," 1966, Nature, vol. 211, pp. 308-309.

Johnson, L.A., "Sex Preselection by Flow Cytometric Separation of X and Y Chromosome-Bearing Sperm Based on DNA Difference: A Review," 1995, Reprod. Fert. Dev., vol. 7, pp. 893-903.

Johnson, L.A., "Sex Preselection: High-Speed Flow Cytometric Sorting of X and Y Sperm for Maximum Efficiency," 1999, Theriogenology, vol. 52(8), pp. 1323-1341.

Lodge, J.R., et al., "Carbon Dioxide in Anaerobic Spermatozoan Metabolism," 1968; vol. 51(1), pp. 96-103.

Salisbury, G.W., Reversal by Metabolic Regulators of CO2-induced Inhibition of Mammalian Spermatozoa, 1959, Proc Soc Exp Biol Med, vol. 101(1), pp. 187-189.

International Search Report for PCT/US2004/009903 dated Aug. 16, 2004, 7 pgs. 7 pages.

International Search Report for PCT/US2005/010598 dated Jun. 27, 2005, 5 pgs.

International Search Report for PCT/US2005/010599 dated Dec. 12, 2005, 9 pgs.

De Pauw, M.C., et al., "Sperm Binding to Epithelial Oviduct Explants in Bulls with Different Nonreturn Rates Investigated with a New in Vitro Model," Biol Reprod, V67, pp. 1073-1079.

Sabeur, K. et al., "Effects of Angiotensin II on the Acrosome Reaction in Equine Spermatozoa," 2000, J Reprod Fert, V120, pp. 135-142.

Millipore Specialty Media, IVF Protocol, http://www.specialtymedia.com/05Resources/Protocols/ivfprotocol.htm.

D'Occhio, M.J., "Sexing of Sperm in Embryos: Use of Sexed Sperm in AI, IVF, ICSI and Graft," 1999, Animal Breeding Use of New Technologies, Kinghorn, van der Werf and Ryan, Eds., Chapter 1, Introduction and Chapter 19, pp. 247-264.

Garner, D.L., et al., "Viability Assessment of Mammalian Sperm Using SYBR-14 and Propidium Iodide," 1995, Biology of Reproduction, vol. 53, pp. 276-284.

Guthrie, H.D., et al., "Flow Cytometric Sperm Sorting: Effects of Varying Laser Power on Embryo Development in Swine," 2002, Molecular Reproduction and Development, vol. 61, pp. 87-92.

Parallel European application No. 05731409.8, Office Action dated Jun. 27, 2007.

Parallel New Zealand applicatin No. 550196; Office Action dated Apr. 10, 2008.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R. P., et al. "Prospects for Sexing Mammalian Sperm," Animal Reproduction Laboratory College of Veterinary Medicine and Biomedical Sciences, Colorado State University. (1982).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Amoah, E. A. and Gelaye, S., "Biotechnological Advances in Goat Reproduction", J. Anim. Sci. 75(2): 578-585. (1996).

Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Baker, R.D., et al., "Effect of Volume of Semen, Number of Sperm and Drugs on Transport of Sperm in Artificially Inseminated Gilts", J. Anim. Sci. 27:88-93. (1968).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).

Bedford, S .J. and Hinrichs, K., "The Effect of Insemination Volume on Pregnancy Rates of Pony Mares", Therio. 42:571-578. (1994).

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Berger, G. S. "Intratubal Insemination", Fertil. Steril. 48:328-330, (1987).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., "Sexual Dimorphism in IVF Bovine Embryos Produced by Sperm Sorted by High Speed Flow Cytometry", abstr. Therio. 49(1): 359 (1998).

Beyhan, Z., Et Al., 1999 Sexual Dimorphism in IVM-IVF Bovine Embryos Produced from X and Y Chromosome-Bearing Spermatozoa Sorted by High Speed Flow Cytometry. Theriogenology. 52: 35-48.

Bigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef—Production III. Culling Strategies and Nontraditional Management-Systems", J. Anim. Sci. 65:963. 1987.

Bracher, V. and Allen, W.R., "Videoendoscopic Examination of the Mare's Uterus: I. Findings in Normal Fertile Mares", Equine Veterinary Journal, vol. 24, p. 274-278. 1992.

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al, "Effect of Different Protein Supplements on Motility and Plasma Membrane Integrity of Frozen- Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.

Brinsko, S.P. et al., "Artificial Insemination and Preservation of Semen." Veterinary Clinics of North America:Equine Practice vol. 8 No. 1 Apr. 1992 pp. 205-218.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.

Buchanan, B.R. "Pregnancy Rates in Mares Following a Single Insemination with a Low Number of Spermatozoa into the Tip of the Uterine Horn" Theriogenology p. 395 1999.

Burns, P. D. and Spitzer, J.C., "Influence of Biostimulation on Reproduction in Postpartum Beef-Cows", J. Anim. Sci. 70:358. 1992.

Burwash, L. D., et al., "Relationship of Duration of Estrus to Pregnancy Rate in Normally Cycling, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

Celestron: Telescope Basics: www.celestron.com/tb-2ref/htm; 4 pages, Oct. 20, 2003.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonoqraphy* 1st ed. Rantanen, N.W. and McKinnon A.O. (eds.) Williams and Williams, 1998, p. 165-69.

da Silva, Coutinho M. A.. "Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

*DakoCytomation, "MoFlo® Sorters"* http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.
Dinnyes, A., et al., "Timing of the First Cleavage Post- Insemination Affects Cryosurvival of In Vitro-produced Bovine Blastocysts", Molec. Reprod. Develop. 53, p. 318-324. 1999.
Dippert, K.D. "Fertilization Rates in Superovulated and Spontaneously Ovulating Mares" Theriogenology 41: 1411-1423, 1994.
Donaldson, L. E., "Effect of Insemination Regimen on Embryo Production in Superovulated Cows", The Veterinary Record, Jul. 13, p. 35-37, 1985.
Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.
Douglas, R. H., "Review of Induction of Superovulation and Embryo Transfer in the Equine" Therio. 11:33-46. 1979.
Douglas, R. H., et al. "Induction of Ovulation and Multiple Ovulation on Seasonally-Anovulatory Mares with Equine Pituitary Fractions." Therio. 2(6): 133-142. 1974.
Doyle, S. P., et al. "Artificial Insemination of Lactating Angus Cows with Sexed Semen". Proc. Western Sect. Am. Soc. Anim. Sci. 50:203. 1999.
Dresser D.W. et at. Analyses of DNA content of Living Spermatozoa Using Flow Cytometry Technique Journal of Reproduction and Fertility, 1993, vol. 98, pp. 357-365.
Duchamp, G., et al. "Alternative Solutions to hCG Induction of Ovulation in the Mare" J. Reprod. Fertil. Suppl. 35:221-228. 1987.
Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.
Ferrell, C. L. Effects of Post-Weaning Rate of Gain on Onset of Puberty and Productive Performance of Heifers of Different Breeds. J. Anim. Sci. 55:1272. 1982.
Ferrell, C. L. and T. G. Jenkins. "Energy-Utilization by Mature, Nonpregnant, Nonlactating Cows of Different Types" J. Anim. Sci. 58:234. 1984.
Field, R. A., et al., "Bone-Ossification and Carcass Characteristics of Wethers Given Silastic Implants Containing Estradiol", J. Anim. Sci. 68:3663-3668. 1990.
Field, R. et al., "Growth, Carcass, and Tenderness Characteristics of Virgin, Spayed, and Single-Calf Heifers", J. Anim. Sci. 74:2178. 1996.
Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.
Fluharty, F. L., et al., "Effects of Age at Weaning and Diet on Growth of Calves",Ohio State University Dept. of Animal Scieneces. 1966 Ohio Agri. Res. and Den. Circular, 156:29 1966.
Foote, et al. Motility and Fertility of Bull Sperm Frozen-Thawed Differently in Egg Yolk and Milk Extenders Containing Detergent, 1987 J Dairy Sci 70:2642-2647.
Foote, R.H., "Buffers and Extenders: What Do They Do? Why Are They Important?" Proc of the NAAB Tech. Conf. on Artificial Insemination and Reproduction, 62-70 (1984).
Foulkes, J. A., et al. "Artificial Insemination of Cattle Using Varying Numbers of Spermatozoa." Vet. Rec. 101:205. 1977.
Francon, M. and Yamamoto, T., "Un Noveau et tres simple dispositif interferentiel applicable as microscope" Optica Acta 9, p. 395-408. 1962.
Fugger, E. F. "Clinical Experience with Flow Cytometric Separation of Human X- and Y-Chromosome Bearing Sperm", Therio. vol. 52, pp. 1435-1440.1999.
Fuller, Robert R. "Characterizing Submicron Vesicles With Wavelenth-Resolved Fluorescence in Flow Cytometry," University of Illinois, May 13, 1996.
Fulwyler, M. J. "Electronic Separation of Biological Cells by Volume." Science. 150:910. 1965.
Fulwyler, M. J. "Hydrodynamic Orientation of Cells." J of Histochem. and Cytochem. 25:781-783. 1977.
Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.
Ginther, O. J., "Some Factors Which Alter Estrus Cycle in Mares." J. Anim. Sci. 33:1158. 1971 abstr.
Ginther, O. J., Reproductive Biology of the Mare. (2nd Ed.) Equiservices, Cross Plains, WI. 1992.
Gledhill, B. L. "Gender Preselection: Historical, Technical and Ethical Perspective." Semen Reprod. Endocrinol. 6:385-395. 1988.
Gombe, S. and Hansel, W. "Plasma Luteinizing Hormone (LH) and Progesterone Levels in Heifers on Restricted Energy Intakes." J. Anim. Sci. 37:728. 1973.
Gottlinger et al., "Operation of a Flow Cytometer", Flow Cytometry and Cell Sorting, A. Radbruch (Ed.), 1992, pp. 7-23.
Gourley, D. D. and Riese, R. L. "Laparoscopic Artificial Insemination in Sheep." Vet. Clin. N. Amer: Food Anim. Prac. 6(3): 615-633 (1990).
Graham, J. Analysis of Stallion semen and its Relation to Fertility. Abstract Complete article from Reproductive Technology vol. 12 # Apr. 1, 1996 now included in XYIDS000213.
Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).
Graham, James K., "Effect of Cholesterol-Loaded Cyclodextrins in Semen Extenders", Proceedings of the 19th Technical Conference on Artificial Insemination & Reproduction, 2003, pp. 91-95.
Gravert, H. O., "Genetic Aspects of Early Calving." In: J.C. Taylor (Ed.) *The Early Calving of Heifers and Its Impact on Beef Production*. 59 (1975).
Gregory, K. E., et al., "Characterization of Biological Types of Cattle—Cycle III: II Growth Rate and Puberty in Females" J. Anim. Sci. 49:461 (1979).
Grimes, I. F, and T. B. Turner. "Early Weaning of Fall Born Calves II. Post Weaning Performance of Early and Normal Weaned Calves". I. Prod. Agric. 4:168 (1991).
Grondahl, C., et al, "In Vitro Production of Equine Embryos", Biology of Reproduction, Monograph Series I, p. 299-307 (1995).
Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).
Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).
Hall, J. B., et al., "Effect of Age and Pattern of Gain on Induction of Puberty with a Progestin in Beef Heifers." J. Anim. Sci. 75:1606 (1997).
Hamamatsu, "*Technical Information, Optical Detector Selection: A Delicate Balancing Act*", web page, http://www.optics.org/hamamatsu/photodiode.html, printed on Apr. 15, 2000, 6 pages total.
Hamano, K., et al., "Gender Preselection in Cattle with Intracytoplasmically Injected, Flow Cytometrically Sorted Sperm Heads", Biology of Reproduction 60, p. 1194-1197 (1999).
Hammerstedt, et al., "Cryopreservation of Mammalian Sperm: What We Ask Them to Survive," Journal of Andrology, 11:1:73-88 (1990).
Harrison, L.A., et al., "Comparison of HCG, Buserelin and Luprostiol for Induction of Ovulation in Cycling Mares." Eq. Vet. Sci. 3:163-166 (1991).
Harte, F. J. "System of Production of Beef From Once Calved Heifers." In: J.C. Taylor (Ed.) *The Early Calving of Heifers and its Impact on Beef Production*. 123 (1975).
Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).
Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.
Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," Sci. Am. 1976; 234, pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine." Science, Oct. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious furo*) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ratio in Semen Purportedly Enriched for X or Y Bearing Spermatozoa", Therio. 1988 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle - Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lightwave Electronics, "Xcyte," www.LightwaveElecronics.com.

Lindsey, A. C., et al., "Low Dose Insemination of Mares Using Non-Sorted and Sex-Sorted Sperm" Animal Reproduction Science 68 p. 279-89 (2001).

Lindsey, A.C. Hysteroscopic insemination of mares with nonfrozen low-dose unsexed or sex-sorted spermatozoa.

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. 2001 abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug in Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy," 1996 Biophotonics International.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production*. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction*. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DNA Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 1971 54:548.

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers—a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Suppl. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female—A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 2001, 23:115-121.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Pickett B.W., et al., Recent Developments in Artificial Inseminatin in Horses Livestock Production Science,1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Nos. and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole *Microtus oregoni*", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115 118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production.* 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) ( 1961 & 1978 Combined) Chapters 16 and 17 are the complete article. Published by W.H.Freeman Co., San Francisco California.

Schenk, J. L. "Applying Sperm Sexing Technology to the AI Industry", Proceedings of the 18th Technical Conference on Artificial insemination & Reproduction, Sep. 29-30, 2000.

Schenk, J. L, et al., "Imminent Commercialization of Sexed Bovine Sperm", Proceedings, The Range Beef Cow Symposium XVI p. 89-96 (1999) Greeley Colorado.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination", 7th International Symposium on Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" the AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Reproductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for in Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., et al, "Insemination of Heifers With Very Low Numbers Of Frozen Spermatozoa", CSU, Atlantic Breeders Cooperative, Lancaster, PA, DUO Dairy, Loveland, CO, Jul. 1996.

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997, Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress on Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com, Copyright 2002.

Spectra-Physics, The Solid State Laser Company, Vanguard 350-HMD 355, www.specra-physics.com Copyright 2002.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", (1998) pp. 1, 39-41, 81-89.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., "Geslachtsbepaling met interferometrie", Derde prijs NtvN-prijsvraag voor pas-gepromoveerden 65/4, (Sex Determination with Interferometry) p. 95-98 (1999).

van Munster, E. B., et al, "Difference in Sperm Head Volume as a Theoretical Basis for Sorting X & Y-Bearing Spermatozoa: Potentials and Limitations", Therio 52, pp. 1281-1293 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Intra Uterine Insemination Technique", Boar Semen Preservation IV, IVth International Conference on Boar Semen Preservation, Maryland, Aug. 8, 1999, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263., Jun. 2004.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Welch G., et al., Fluidic and Optical Modifications to a FACS IV for Flow Sorting of X- and Y-Chromosome Bearing Sperm Based on DNA. Cytometry 17 (Suppl. 7): 74. (1994).

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wheeler, T. L., et al., "Effect of Marbling Degree on Beef Palatability in *Bos-taurus* and *Bos-indicus* cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Hamamatsu, "*Photomultiplier Tubes*," web page, http://www.optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1995).

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology , vol. 59. (2003) pp. 209.

Dhali et al. Vitrification of Buffalo (*Bubalus bubalis*)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for in Vitro fertiliation and Al, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y- chromosome bearing sperm, Cytometry 25:191-199 (1996).

van Munster, E. B. Interferometry in flow to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/Isrll.htm, pp. 14, May 11, 2004.

Saacke, R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low Numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation in First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $in Asia B. Japan; www.agnet.org/library/article/eb384b.html.

Crichton, E. et al., 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept of Agri.

De Vries, A. Economic Value of Pregnancy in Dairy Cattle Journal of Dairy Sci. 89:3876-3885/American Dairy Sci. Assoc. 2006.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel *Anguilla japonica*, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and -D-Glucuron idase Activity as Indicators of Sea Bass Semen Quality; Biology of Reproduction 70,1679-1684 (2004).

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228 237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (*Anser anser* L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18(2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffaloes (*Bubalus bubalis*) following deposition of sexed spermatozoa near the utero tubal junction, Reproduction in Domestic Animals, vol. 40, No. 1, Feb. 2005 , pp. 73-75(3).

Dielemann, S.J., Superovulation in cattle: from understanding the biological mechanisms to genomics of the oocyte; $23^{rd}$ Annual Meeting A.E.T.E.—Alghero; Sep. 2007.

Hasler, J. F., Factors influencing the success of embryo transfer in cattle; $23^{rd}$ World Buiatrics Congress, Quebec, Canada Jul. 2004.

Mapletoft, R. J. et al., Superovulation in perspective, Bioniche Animal Health, Dec. 2002.

Bahr, G.F.et al., Considerations of volume, mass, DNA, and arrangement of mitochondria in the midpiece of bull spermatozoa, Experimental Cell Research 60 (1970) 338-340.

BD LSR II Flow Cytometer, BD Biosciences Clontech Discovery labware Immunocytometry systems Pharmingen Jan. 28, 2004.

Bermudez, D.et al., The immediate effect of IR, laser radiation on rat, germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Brooks, D.E., Manipulation of Mammalian Gametes in Vitro, Biennial Report, Waite Agricultural Research Institute 1986-1989.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.

Chen, Y. et al., Effects of sucrose, trehalose, hypotaurine, taurine, and blood serum on survival of frozen bull sperm, Cryobiology 30,423-431 (1993).

Chapter 16 Semen processing, storage, thawing, and handling, http://nongae.gsnu.ac.kr/~cspark/teaching/chap16.html Sep. 23, 2002.

Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Certified Semen Services, CSS Minimum requirements for disease control of semen produced for AI, http://www.naab-css.org/about_css/disease_control-2002.html Sep. 22, 2003.

Culling, "Handbook of Histopathological and Histochemical Techniques,"3rd Ed., Butterworths, pp. 192.

De Grooth, B. et al., Simple delay monitor for droplet sorters, Cytometry 12:469-472 (1991).

Delgado,N. et al., Correlation between sperm membrane destabilization by heparin and aniline blue staining as membrane integrity index, Archives of Andrology40:147-152 (1998).

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antibiotic Combination", Theriogenology, 1990, vol. 33(6), pp. 1211-1220.

Cho, et al. A microfluidic device for separating motile sperm from nomotile sprem via inter-streamline crossings.

Ericsson, R. et al., Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Fitzgerald, D., Cell sorting: An enriching Experience, The Scientist Jul. 23, 2001.

Foote,R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel,D.et al.,Flow cytometry of mammalian sperm progress in DNA and morphology measurement, The Journal of Histochemical and Cytochemistryvol.27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Centola, G.et al., Cryopreservation of human semen. Comparison of cryopreservatives, sources of variability, and prediction of post-thaw survival. PMID: 1601749 May-Jun. 1992.

Courtens, J. et al., Numerical simulation for freezing and thawing mammalian spermatozoa. Evaluation of cell injuries at different depths in bags or straws during all steps of the technique.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Young, L.et al., Prolonged feeding of low levels of zearalenone to young boars.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 06, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al., Spermatozoa and Seminal Plasma, Reproduction in farm animals 7th edition.

Gadella B,et al., Dynamics in the membrain organization of the mammalian sperm cell and functionality in fertilization, Vet Quart. 21:142-146 (1999).

Garner, D.et al., Chromatin stability in sex-sorted sperm, VII International Congress of Andrology.

Garner, D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., "Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2879 (1992).

Held, A.et al., Quasi- CW Solid- state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish AI bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement , Sep. 4, 1990.

Johnson, L., Flow sorting of intact X & Y chromosome-bearingmammalian spermatozoa, The Journal of the Society for Analytical Cytology Cytometry, (1988).

Zhang,M. et al., Development of bovine embryos after in vitro fertilzation of oocytes with a flow cytometrically sorted, stained and unsorted sperm from different bulls, Theriogenology 60: 1657-1663 (2003).

Jones,R.et al., Effect of Osmolality and Phosphate, "Tris", "Tes", "Mes", nd "Herpes" Hydrogen ion buffers on the motility of bull spermatozoa stored at 37 or 5° C., Ausi J. Biol. Sci.25:1047-1055 (1972).

Jones,R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland.

Johnson, L., Separation of X and Y Chromosome-bearing mammalian sperm by DNA content cytometric analysis and sorting, US Department of Agriculture.

Johnson, M.,The Macromolecular Organization of membranes and its bearing on events leading up to Fertilization, Journal of Reproduction and Fertility (1975).

Johnson, L., Verified Sex Pre-Selection in Farm Animals.

Johnson, L., Prograss towards achieving sex preselection in farm animals, USDA Agricultural Research Service, (1989).

Keeler, K.et al., Flow microfluorometric analysis of living spermatozoa stained with Hoechst 33342, J. Reprod.Fert. 68:205-212 (1983).

Keij, J.et al., High speed Photodamage cell sorting: An evaluation of the Zapper Prototype, Methods in cell Biology vol. 42, (1994).

Kirchhoff, C.et al., The Molecular biology of the sperm surface:Post-Testicular Membrane Remodelling, The Fate of the Male Germ Cell, (1997).

Krueger, C.et al.,Low dose Insemination in synchronized gilts, Theriogenology 52: 1363-1373 (1999).

Landetie,J.,Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J.et al., Orientation measurments of microsphere doublets and metaphase chromosomes in flow, Cytometry 7:575-581 (1986).

Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Masaki, J.et al., Effect of bull seminal plasma on the membrane characteristics of boarepididymal spermatozoa.

Maxwell, W.et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney,K.et al., Abstract: Insemination of lactating holstein cows with sexed frozen/thawed sperm, http://www.cvmbs.colostate.edu/physio/abstract/ges12.html Mar. 16, 2004.

Medeiros,C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M.et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al.,"Sexing of Sperm by Flow Cytometry", The Veterinary Record, 1988, pp. 322-324.

Morrier, A.et al., Glycerol addition and conservation of fresh and crypreserved ram spermatozoa, Canadian Journal of AnimalScience, Sep. 2002http://pubs.nrc-cnrc.gc.ca/aic-journals/2002ab/cjas02/sep02/cjas01-045.html.

Moruzzi, J., Selecting a mammalian species for the separationof X- and Y- chromosome-bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R& D Magazine, Dec. 2003: pp. 36-37 as currently presented on and printed from http;//www.rdmag.com 2 pgs.

Gwo-Bin, L.et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983,pp. 11-19,4,Allan R. Liss, Inc.

OcanaQuero, J.et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med.J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R.et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research an International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Polge, C., Low-temperature storage of mammalian spermatozoa, Unit of Reproductive Physiology and Biochemistry, Cambridge.

Edited by Bell-Prince, C. , NFCR Newsletter, http://www.Is.lanl.gov/NFCR/newsletter-Oc98/oct98.html Jan. 6, 2004.

Rasul, Z.et al., Changes in motion characteristics, plasma membrane integrity, and acrosome morphology during cryopreservation of buffalo spermatozoa, Journal of Andrology, vol. 22 No. 2, 3-4 (2001).

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes-Mereno, C.et al., Characterization of Secretory Proteins from cultured Cauda Epididymal Cells that significantly sustain bovine sperm motility, Molecular Reproduction and Development 63: 500-509 (2002).

Rippel,N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Schroter, S.et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart,R., Georgia Beef Challenge, Livestock Newsletter 1-2 (2002).

Takacs, T.et al.,Flow Cytometric determination of the sperm cell number in diluted bull semen samples by DNA staining method, Acta Biochim.Biophys.Hung. vol. 22 No.1, pp. 45-57 (1987).

Thurston,L. et al., Identification of Amplified restriction fragment length polymorphism markers linked to genes controlling boar sperm viability following cryopreservation, Biology Of Reproduction 66: 545-554 (2002).

Tone,S.et al., A method of vital staining of mouse eggs using Hoechst dye, Department of Developmential Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch,G.et al., Sex preselection: Laboratory Validation of the sperm sex ratio of Flow sorted X- and Y- sperm by sort reanal ysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during in vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.

XY, Inc., Sex selection Procedure, http://www.xyinc.com/sex select. html, Feb. 21, 2003.
XY Files, Issue 4 Aug. 2000.
XY Files, Issue 2 Oct. 1999.
XY Files, Issue 3 Mar. 2000.
XY Files, Issue 5 Mar. 2001.
XY Files, Issue 6 Mar. 2002.
Lindsey, A. C., et al., Hysteroscopic inseminatin of mares with low numbers of nonsorted or flow sorted spermatozoa; Equine vet. J. (2002) 34(2) 128-132.
Sharpe, Johnathan, Advances in flow cytometry for sperm sexing, Unpublished paper, 2008.
Johnson, S.K., Possibilities with today's reproductive technologies. Available online at www.sciencedirect.com; Therio 64(2005) pp. 639-656.
Brogliatti, G. et al., Pregnancy Rates and First Born Calves by Artificial Insemination using Sexed Semen in Argentina: Therio. Jan. 2, 2002, vol. 57, No. 1 . p. 369.
Palma, G. et al., Sperm Physiology: The Ability to Produce Embryos In Vitro using Semen from Bulls with a Low Non-Return Rate. Therio. p. 308.
Gottlinger, Christopher et al., Cell-Cooling in Flow Cytometry by Peltier Elements. Cytometry 7:295-297 (1986).
Abstracts: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.
Argentine Patent Application No. P05 01 01214 filed Mar. 30, 2005; Translation of Opposition filed by XY, Inc. on Oct. 6, 2006.
Parallel Chinese Application No. 200580017370.5; Office Action dated Oct. 17, 2008.
Lindsey, A. L., et al., Hysteroscopic or rectally guided, deep-uterine insemination of mares with spermatozoa stored 18 h at either 5° C. or 15° C. prior to flow-cytometric sorting, Animal Reproduction Science, vol. 85, Issues 1-2, Jan. 2005, pp. 125-130.
Schenk, J. L., et al., Pregnancy rates in heifers and cows with cryopreserved sexed sperm: Effects of sperm numbers per inseminate, sorting pressure, and sperm storage before sorting, Theriogenology (2008), doi:10.1016/j. theriogenolology. 2008:08:016.
Suh, T.K., et al., High pressure flow cytometric sorting damages sperm, Theriogenology 64 (2005) 1035-1048.
Upreti, G. C., et al., Studies on aromatic amino acid oxidase activity in ram spermatozoa: role of pyruvate as an antioxidant, Animal Reproduction Science 51 (1998) 275-287.
Schafer, D. J., et al., comparison of progestin-based protocols to synchronize estrus and ovulation before fixed-time artificial insemination in postpartum beef cows, Journal of Animal Science Mar. 30, 2007, pp. 1-21.
Lamb, G. C., Synchronization of estrus and artificial insemination in replacement beef heifers using gonadotropin-releasing hormone, prostaglandin F2a and progesterone, Journal of Animal Science Nov. 1, 2006, vol. 84, pp. 3000-3009.
Saladarriaga, J. P., Ovarian, hormonal, and reproductive events associated with synchronization of ovulation and timed appointment breeding in *Bos indicus*-influenced cattle using intravaginal progesterone, gonadotropin-releasing hormone, and prostaglandin F2a, Journal of Animal Science Jan. 2007, vol. 85, pp. 151-162.
O'Brien, J. K. et al., Semen collection, characterization an preservation in a beluga (*Delphinapterus leucas*), 1st International workshop on Beluga whale research, husbandry and management in wild and captive environments Mar. 2007.
O'Brien, J. K. et al., Development of sperm sexing and associated assisted reproductive technology for sex preselection of captive bottlenose dolphins (*Tursiops truncatus*), Reproduction, Fertility and Development 2008, 18, 319-329.
Parallel U.S. Appl. No. 11/192,338, Office action dated Jun. 24, 2009.
Parallel U.S. Appl. No. 11/192,338, Office action dated Sep. 26, 2008.
Parallel AU Application No. 2005229073, Office action dated Aug. 27, 2009.
Parallel CN Application No. 200580017376.2, Office action dated Mar. 13, 2009.
Parallel CN Application No. 200580017370.5, Office action dated Mar. 8, 2009.
Parallel CN Application No. 200580017370.5, Office action dated Oct. 17, 2008.
Parallel EP Application No. 05731409.8, Office action dated Jun. 27, 2007.
Parallel EP Application No. 05731409.8, Office action dated Jul. 3, 2009.
Biewenga et al., The Pharmacology of the Antioxidant Lipoic Acid, General Pharmacology, vol. 29, p. 315-331, 1997.
Geva et al., Free radicls, antioxidants and human spermatozoa: clinical implications, Human Reproduction, vol. 13, p. 1422-1424, 1998.
Wang et al., Reactive Oxygen species generation by seminal cells during crypreservation, Urology, vol. 49, p. 921-925, 1997.
Packer et al., Alpha-lipoic acid as a biological antioxidant, Free radical biology & medicine, vol. 19, p. 227-250, 1995.
Andrabi, et al. Effect of Reducing Sperm Numbers Per Insemination Dose on Fertility of Cryopreserved Buffalo Bull Semen, Pakistan Vet. J., 2006, 26(1): 17-19.
Tardif et al., Use of Hoechst 33342 stain to evaluate live fresh and frozen bull sperm by computer-assisted analysis, Journal of Andrology, vol. 19, No. 2, 1998 p. 201-206.
De Ambrogi, M.et al., Effect of storage in short- and long-term commercial semen extenders on the motility, plasma membrane and chromatin integrity of boar spermatozoa, International Journal of Andrology (2006) 543-552.
Sa-Ardrit, M. et al., Ultrastructural alterations of frozen-thawed Asian elephant (*Elephas maximus*) spermatozoa, International Journal of Andrology (2006) 346-352.
Coulter Electronics, Inc., Hialeah, FL 33010, (now: Beckmann Coulter International), Coulter Epics V System, Product Reference Manual, Apr. 1984.
Meneze, Y, et al. Serum is not necessary in human in vitro fertilization, early embryo culture and transfer, Fertility and Sterility, The American Fertility Society, vol. 42, No. 3, Nov. 1984.
Corning Glass. Surface Areas and Recommended Medium Vol. for Corning Cell Culture Vessels./ Life Sciences/Costar 48 Well Clear TC-Treated Microplates 2009.
Auger, Jacques, et al. Flow Cytometric Sorting of Living, Highly Motile Human Spermatozoa Based on Evaluation of Their Mitochondrial Activity. The Journal of Histrochemistry and Cytochemistry. vol. 41 pp. 1247-1251. 1993.
Bencic, D.C., et al. "Carbon Dioxide Reversibly Inhibits Sperm Motility and Fertilizing Ability in Steelhead (*Oncorhynchus mykiss*)," Fish Phys. And Biochem., 2000, vol. 23, pp. 275-281.
Boatman D.E., et al., "Bicarbonate: Carbon-Dioxide Regulation of Sperm Capacitation, Hyperactivated Motility, and Acrosome Reactions," Biol. of Reprod., 1991, vol. 44, pp. 806-813.
International Search Report for PCT/US2005/010481, dated Oct. 10, 2005, 6 pages.
Z. Liu and R.H. Foote, Bull Sperm Motility and Membrand intrgrity in Media Varying In Osmolality, J Dairy Sci vol. 81 pp. 1886-1874 (1998).
Parallel U.S. Appl. No. 11/192,339 office action dated Mar. 19, 2010.
Parallel CN Application No 200580017370.5 office action dated Nov. 13, 2009.
Parellel CN Application No. 200580017370.5 office action dated Apr. 15, 2010.
Parallel NZ Application No. 550196 office action dated Apr. 21, 2010.
Parallel EP Application No. 09014128.4 office action dated Feb. 3, 2010.
Parallel CN Application No. 200580017376.2 office actiion dated Feb. 24, 2010.
Parallel NZ Application No. 581168 office action dated Nov. 19, 2009.
Parallel AU Application No. 2005229073 office action dated May 20, 2010.
Parallel AR Application No. P050101214 office action dated May 5, 2009.
Parallel AR Application No. P0501214 office action dated Nov. 4, 2009.

Parallel AU Application No. 2005228893 office action dated Sep. 16, 2009.

Parallel NZ Application No. 550196 office action dated Apr. 10, 2008.

Parallel NZ Application No. 550196 office action dated Oct. 8, 2008.

Vervoort et al., The Potent Antioxidant Activity of the Vitamin K Cycle in Microsomal Lipid Peroxidation, Biochemical Pharmacology vol. 54, pp. 871-876 (1997).

Garner et al. Effect of Semen Dilution on Bovine Sperm Viability as Determined by Dual-DNA Staining and Flow Cytometry, J Androl 18:324-331 (1997).

Bavister, A consistently Successful Procedure for In Vitro Fertilization of Golden Hamster Eggs, Gamete Research 23:139-158 (1989).

Bavister, Barry D., Consistently Successful Procedure for In-Vitro Fertilization of Golden Hamster Eggs, Gamete Research, vol. 23, pp. 139-159,1989.

Chinese Office Action dated Dec. 11, 2009 for CN parallel application No. 200580017370.5.

New Zealand Exam Report dated Dec. 11, 2009 for NZ patent application No. 550196.

Argentina Exam Report dated Nov. 4, 2009 for AR parallel application P050101214.

Australian Office Action dated May 20, 2010 in parallel application No. 2005229073.

EP search Report Written Opinion dated Jan. 7, 2010 for parallel EP application No. 09014128.4.

SPERM SUSPENSIONS FOR SORTING INTO X OR Y CHROMOSOME-BEARING ENRICHED POPULATIONS

REFERENCE TO RELATED APPLICATIONS

This application is a nonprovisional of and claims the priority to U.S. Patent Application Ser. No. 60/557,407, filed Mar. 29, 2004, U.S. Patent Application Ser. No. 60/614,178, filed Sep. 29, 2004, and U.S. Patent Application Ser. No. 60/618,440, filed Oct. 13, 2004, the content of each of which is hereby incorporated herein by reference in its entirety.

FIELD OF THE INVENTION

The present invention generally relates to a process of sorting sperm cells. More specifically, the present invention relates to the preparation of suspensions of sperm cells having reduced motility, and more particularly a temporarily reduced motility, relative to endogenous ejaculated sperm, the suspensions having utility, for example, in a process for sorting sperm cells into an enriched population of X or Y chromosome-bearing sperm cells.

BACKGROUND

The fertilization of animals by artificial insemination (AI) and embryo transplant following in vitro fertilization is an established practice. In the livestock production industry, the ability to influence the reproductive outcome toward offspring having one or more desired characteristics has obvious advantages. By way of example, there would be an economic benefit in the dairy industry to preselect offspring in favor of the female sex to ensure the production of dairy cows. The separation of sperm into enriched populations of X and Y chromosome-bearing cells, known as gender enriched semen or gender enriched sperm, is one method of achieving preselected offspring.

In order to obtain gender enriched semen, sperm cells must be stained with a dye and subsequently sorted into X and Y chromosome-bearing cells. Each of staining and sorting processes places a stress on the sperm cells that decreases sperm cell viability or motility, particularly progressive motility.

Salisbury et al. describe a technique for the collection of ejaculated bovine semen directly into a diluent which inhibits cell motility and prevents the absorption of carbohydrates from the surrounding seminal plasma. When the ejaculate is collected into the diluent and the air phase above the liquid is replaced by gassing with 100% $CO_2$, the cells in the ejaculate became immotile. As long as the cells remained in the diluent and air was excluded, the cells remained immotile for several hours at room temperature and for at least 8 days at 5° C.

SUMMARY OF THE INVENTION

Among the various aspects of the present invention are sperm suspensions having utility, for example, in processes used to sort sperm into enriched populations of X or Y-chromosome bearing sperm.

Briefly, therefore, the present invention is directed to a sperm cell suspension comprising viable spermatozoa and a composition which down-regulates carbohydrate uptake by the spermatozoa, the concentration of spermatozoa in the suspension being less than about $1 \times 10^6$ or at least $1 \times 10^8$ spermatozoa per ml.

The present invention is further directed to a sperm cell suspension comprising viable, immotile sperm, the concentration of spermatozoa in the suspension being less than about $1 \times 10^6$ or at least $1 \times 10^8$ spermatozoa per ml.

The present invention is further directed to a sperm cell suspension comprising viable spermatozoa, the spermatozoa having a motility more characteristic of epididymal spermatozoa than endogenous ejaculated spermatozoa of the same species, the concentration of spermatozoa in the suspension being less than about $1 \times 10^6$ or at least $1 \times 10^8$ spermatozoa per ml.

The present invention is further directed to a sperm cell suspension comprising viable sperm, potassium and optionally sodium, the concentration of spermatozoa in the suspension being at least $1 \times 10^8$ spermatozoa per ml and the molar ratio of potassium to sodium being greater than 1:1, respectively.

The present invention is further directed to a sperm cell suspension comprising viable spermatozoa, a composition which down-regulates carbohydrate uptake by the spermatozoa, and a DNA-selective dye.

The present invention is further directed to a sperm cell suspension comprising viable, immotile sperm and a DNA-selective dye.

The present invention is further directed to a sperm cell suspension comprising viable spermatozoa and a DNA-selective dye, the spermatozoa having a metabolic rate and motility more characteristic of epididymal spermatozoa than endogenous ejaculated spermatozoa of the same species.

The present invention is further directed to a sperm cell suspension comprising viable, immotile spermatozoa, the spermatozoa having a DNA-selective dye associated with their DNA.

The present invention is further directed to a sperm cell suspension comprising viable spermatozoa, the spermatozoa having a metabolic rate and motility more characteristic of epididymal spermatozoa than endogenous ejaculated spermatozoa of the same species, the spermatozoa also having a DNA-selective dye associated with their DNA.

The present invention is further directed to a process for staining sperm cells, the process comprising forming a staining mixture containing intact viable sperm cells, a motility inhibiting amount of potassium, and a DNA selective dye.

The present invention is further directed to a process of forming a sperm cell suspension for use in a flow cytometry process, the process comprising combining a sperm cell source with a composition which inhibits the motility of sperm cells to form a sperm cell suspension, the concentration of sperm cells in the suspension being less than about $1 \times 10^6$ or at least $1 \times 10^8$ sperm cells per milliliter.

The present invention is further directed to a process of forming a sperm cell suspension for use in a flow cytometry process, the process comprising collecting the ejaculate of a mammal in a buffer containing an inhibitory amount of a motility inhibitor to form a sperm cell suspension, the suspension comprising less than about $1 \times 10^6$ or at least $1 \times 10^8$ sperm cells per milliliter.

Other aspects and features of the invention will be in part apparent and in part pointed out hereinafter.

DETAILED DESCRIPTION OF THE INVENTION

Figure 1:
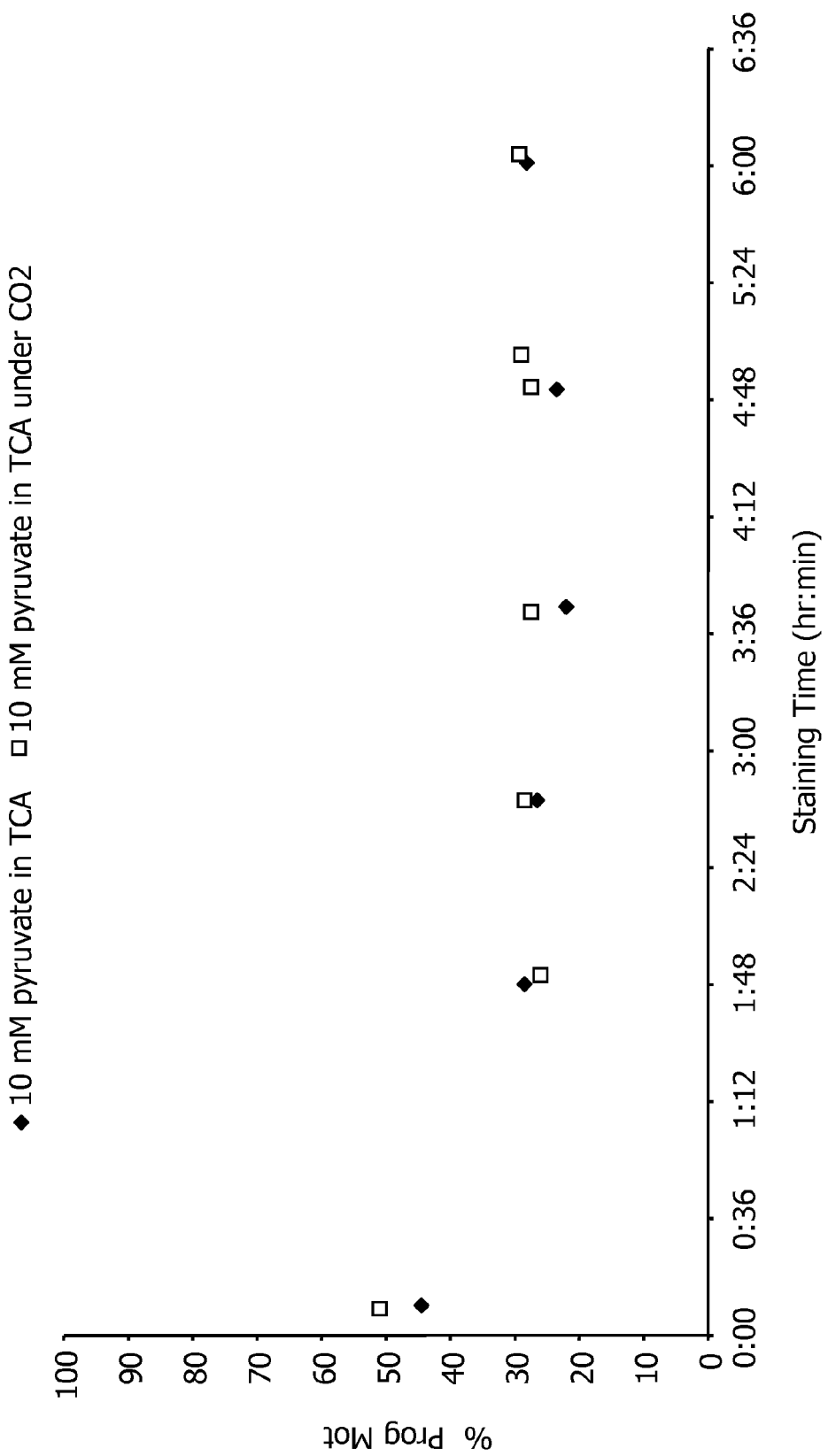
FIG. 1 graphically depicts the results of the study carried out in Example 1 wherein percent progressive motility of sperm cells is measured for sperm cells stained with 600 μM Hoechst 33342 dye at 28° C. in TCA containing 10 mM pyruvate or in carbon dioxide-blanketed TCA containing 10 mM pyruvate.

Surprisingly, it has been determined that spermatozoa having reduced motility relative to endogenous ejaculated spermatozoa (of the same species) tend to have a greater capacity for enduring the various process steps typically associated with the sorting of sperm cells into an enriched population of X or Y chromosome-bearing spermatozoa. In a preferred embodiment, therefore, gender enriched populations of spermatozoa may be prepared for artificial insemination which have an increased number of viable cells or an increased number of motile sperm, particularly progressively motile sperm, in a post-stain or post-sort composition.

In accordance with the process of the present invention, a suspension, sometimes referred to as a dispersion, is formed containing spermatozoa and one or more compositions which inhibit the motility of the spermatozoa; such a state of inhibited motility sometimes being referred to as immotility or sperm quiescence. In general, the suspensions will contain spermatozoa in a density of about $1 \times 10^3$ sperm/ml to about $5 \times 10^{10}$ sperm/ml of suspension. For example, in one embodiment the suspensions may contain spermatozoa in a "relatively low" density, i.e., in a density of less than about $1 \times 10^7$ sperm/ml, preferably less than about $1 \times 10^6$ sperm/ml, more preferably about $1 \times 10^3$ to about $5 \times 10^6$ sperm/ml, still more preferably about $1 \times 10^3$ to about $1 \times 10^6$ sperm/ml, even more preferably about $1 \times 10^4$ to about $1 \times 10^5$ sperm/ml, and most preferably about $1 \times 10^5$ sperm/ml of suspension. In an alternative embodiment, the suspensions may contain spermatozoa in an "intermediate" density, i.e., in a density of about $1 \times 10^7$ to about $1 \times 10^8$ sperm/ml of suspension. In yet another alternative embodiment, the suspensions may contain spermatozoa in a "relatively high" density, i.e., in a density of at least about $1 \times 10^8$ sperm/ml, preferably about $1 \times 10^8$ to about $5 \times 10^{10}$ sperm/ml, more preferably about $1.5 \times 10^8$ to about $2 \times 10^{10}$ sperm/ml, even more preferably about $1.5 \times 10^8$ to about $2 \times 10^8$ sperm/ml, and still more preferably about $1.5 \times 10^8$ sperm/ml of suspension. Thus, for example, in one embodiment the suspension may contain at least about $1.25 \times 10^8$, at least about $1.5 \times 10^8$, at least about $1.75 \times 10^8$, at least about $2 \times 10^8$, at least about $2.25 \times 10^8$, at least about $2.5 \times 10^8$, at least about $2.75 \times 10^8$, or even at least about $3 \times 10^8$ sperm/ml of suspension. In an alternative embodiment, the suspension may contain less than about $9 \times 10^5$, less than about $7 \times 10^5$, less than about $5 \times 10^5$, less than about $2 \times 10^5$, less than about $1 \times 10^5$, less than about $1 \times 10^4$, or even less than about $1 \times 10^3$ sperm/ml of suspension.

The density of spermatozoa in the sperm suspensions depends upon several considerations, including the method by which the sperm cells may be subsequently enriched or sorted. For example, the sperm cells may be sorted using flow cytometry as described in greater detail below. In such an instance, the buffered sperm suspension may typically be of an "intermediate" or "relatively high" density of spermatozoa. Other sorting or enrichment techniques may benefit from a lesser density of spermatozoa, such as a "relatively low" density of spermatozoa, labeled with a marker, such as for example the dyes and labels described herein.

In a preferred embodiment, spermatozoa in suspensions of the present invention behave, in certain respects, in a manner characteristic of epididymal spermatozoa; for example, the spermatozoa may be immotile and/or they may have a lesser rate of endogenous respiration and a greater rate of aerobic glycolysis as compared to washed or freshly ejaculated spermatozoa. Advantageously, the inhibited spermatozoa have the ability, upon separation from the inhibitor(s), to behave in a manner characteristic of ejaculated spermatozoa (and not characteristic of epididymal spermatozoa) with respect to motility and, in one embodiment, with respect to motility and respiration.

In one embodiment, for example, the motility inhibitor reduces path velocity, progressive velocity, or both, as measured by HTM-IVOS sperm analysis (Hamilton-Thorne HTM-IVOS computer assisted sperm analysis system Hamilton-Thorne Research, Beverly Mass.) of at least about 50% of the sperm cells in the dispersion relative to the path velocity, progressive velocity, or both of sperm cells in a fresh ejaculate of the same species. Preferably, the motility inhibitor reduces path velocity, progressive velocity, or both, as measured by HTM-IVOS sperm analysis, of at least about 60% of the sperm cells in the dispersion relative to the path velocity, progressive velocity, or both of sperm cells in a fresh ejaculate of the same species. More preferably, the motility inhibitor reduces path velocity, progressive velocity, or both, as measured by HTM-IVOS sperm analysis, of at least about 70% of the sperm cells in the dispersion relative to the path velocity, progressive velocity, or both of sperm cells in a fresh ejaculate of the same species. Still more preferably, the motility inhibitor reduces path velocity, progressive velocity, or both, as measured by HTM-IVOS sperm analysis, of at least about 80% of the sperm cells in the dispersion relative to the path velocity, progressive velocity, or both of sperm cells in a fresh ejaculate of the same species. Even more preferably, the motility inhibitor reduces path velocity, progressive velocity, or both, as measured by HTM-IVOS sperm analysis, of at least about 90% of the sperm cells in the dispersion relative to the path velocity, progressive velocity, or both of sperm cells in a fresh ejaculate of the same species. Even more preferably, the motility inhibitor reduces path velocity, progressive velocity, or both, as measured by HTM-IVOS sperm analysis, of at least about 95% of the sperm cells in the dispersion relative to the path velocity, progressive velocity, or both of sperm cells in a fresh ejaculate of the same species. Most preferably, the motility inhibitor reduces path velocity, progressive velocity, or both, as measured by an HTM-IVOS sperm analysis, of at least about 99% of the sperm cells in the dispersion relative to the path velocity, progressive velocity, or both of sperm cells in a fresh ejaculate of the same species.

In addition to or in lieu of an inhibitory buffer, the temperature of the sperm cells or the immediate environment surrounding the sperm cells (i.e., a sperm dispersion) may solely be reduced to affect the motility of the cells. Such a reduction in temperature will generally increase immotility. Moreover, for example, the reduction of temperature of the sperm cells or the sperm dispersion may permit a reduction in the concentration of inhibitor used to induce immotility. Accordingly, the sperm dispersion may be at a temperature not in excess of 5° C.; preferably between about 0° C. and about 5° C.; more preferably between about 3° C. and about 5° C.; and most preferably about 5° C. Alternatively, the sperm dispersion may be at a temperature within the range of about 4° C. to about 50° C.; preferably from about 7° C. to about 43° C.; more preferably from about 10° C. to about 39° C.; still more preferably from about 15° C. to about 30° C.; even more preferably from about 17° C. to about 25° C.; and most preferably at about 18° C. Preferably, however, the sperm cells are not exposed to temperatures that substantially detrimentally affect the viability of the cells.

The inhibitor may be any of a range of compositions having a depressive effect upon sperm motility. Such compositions include, for example, sodium/potassium ATPase inhibitors, such as, ouabain; compositions comprising potassium ions; and compositions comprising potassium and sodium ions. For example, relatively high concentrations of potassium ions in the suspension tend to depress sperm motility. In general, therefore, it is preferred that the suspension contain a source of potassium ions and that the potassium concentration in the suspension be at least about 0.05 moles/L. More preferably, the potassium concentration is at least about 0.05 moles/L to about 0.5 moles/L. Still more preferably, the potassium concentration is at least about 0.1 moles/L to about 0.3 moles/L. Most preferably, the potassium concentration is at about 0.173 moles/L. Such suspensions will typically, but not necessarily, also contain a source of sodium ions. When sodium is present, the molar ratio of potassium to sodium is generally equal to or greater than 1:1, respectively. Preferably, the molar ratio of potassium to sodium is at least about 1.25:1. Still more preferably, the molar ratio of potassium to sodium is at least about 1.5:1. Still more preferably, the molar ratio of potassium to sodium is at least about 1.75:1. Still more preferably, the molar ratio of potassium to sodium is at least about 1.78:1. In one particular embodiment, the molar ration of potassium to sodium is at least about 2:1. In yet another embodiment, the molar ratio of potassium to sodium is at least about 3:1. In still another embodiment, the molar ratio of potassium to sodium is at least about 4:1. In still another embodiment, the molar ratio of potassium to sodium is at least about 5:1. In still another embodiment, the molar ratio of potassium to sodium is at least about 6:1. In still another embodiment, the molar ratio of potassium to sodium is at least about 7:1. In still another embodiment, the molar ratio of potassium to sodium is at least about 8:1.

The sperm suspension may additionally comprise an ion or source of carbon dioxide capable of down-regulating uptake of carbohydrate. In this embodiment, the source of carbon dioxide may be, for example, one or more carbonates. In one presently preferred embodiment, the sperm suspension comprises $NaHCO_3$ and $KHCO_3$, thereby providing a source potassium and sodium ions as well as a partial pressure of carbon dioxide. For example, in one presently preferred embodiment, the suspension comprises $NaHCO_3$ and $KHCO_3$ in an aqueous solution, preferably $NaHCO_3$, $KHCO_3$, and $C_6H_8O_7.H_2O$ in water; in general, the $KHCO_3$ concentration in the dispersion may be at least about 0.05 moles/L. More preferably, the $KHCO_3$ concentration is at least about 0.05 moles/L to about 0.5 moles/L. Still more preferably, the $KHCO_3$ concentration is at least about 0.1 moles/L to about 0.3 moles/L. In one particularly preferred embodiment, the suspension is formed using an inhibitory buffer comprising 0.097 moles/L of $NaHCO_3$, 0.173 moles/L of $KHCO_3$, 0.090 moles/L $C_6H_8O_7.H_2O$ in water as disclosed in Salisbury & Graves, *J. Reprod. Fertil.*, 6:351-359 (1963). The sperm cells will generally remain quiescent as long as they are exposed to the motility inhibitor(s).

When $C_6H_8O_7.H_2O$ is present in the dispersion, the molar ratio of $KHCO_3$ to $NaHCO_3$ may be as described above. The molar ratio of $KHCO_3$ to $C_6H_8O_7.H_2O$ may generally be equal to or greater than 1:1, respectively, but will generally not exceed a molar ratio of 8:1. Preferably, the molar ratio of $KHCO_3$ to $C_6H_8O_7.H_2O$ is from at least about 1.25:1. Still more preferably, the molar ratio of $KHCO_3$ to $C_6H_8O_7.H_2O$ is at least about 1.5:1. Still more preferably, the molar ratio of $KHCO_3$ to $C_6H_8O_7.H_2O$ is at least about 1.75:1. In one particular embodiment, the molar ratio of $KHCO_3$ to $C_6H_8O_7.H_2O$ is at least about 1.78:1. In another particular embodiment, the molar ratio of $KHCO_3$ to $C_6H_8O_7.H_2O$ is at least about 2:1. In yet another embodiment, the molar ratio of $KHCO_3$ to $C_6H_8O_7.H_2O$ is at least about 3:1. In still another embodiment, the molar ratio of $KHCO_3$ to $C_6H_8O_7.H_2O$ is at least about 4:1. In still another embodiment, the molar ratio of $KHCO_3$ to $C_6H_8O_7.H_2O$ is at least about 5:1. In still another embodiment, the molar ratio of $KHCO_3$ to $C_6H_8O_7.H_2O$ is at least about 6:1. In still another embodiment, the molar ratio of $KHCO_3$ to $C_6H_8O_7.H_2O$ is at least about 7:1. In still another embodiment, the molar ratio of $KHCO_3$ to $C_6H_8O_7.H_2O$ is at least about 8:1. In one particularly preferred embodiment, the dispersion is formed using an inhibitory buffer comprising 0.097 moles/L of $NaHCO_3$, 0.173 moles/L of $KHCO_3$, 0.090 moles/L $C_6H_8O_7.H_2O$ in water as disclosed in Salisbury & Graves, *J. Reprod. Fertil.*, 6:351-359 (1963). The sperm cells will generally remain quiescent as long as they are exposed to the motility inhibitor(s).

Experimental evidence to date further suggests that the overall health and other vital characteristics of sperm cells may be improved if the cell suspension is maintained under an atmosphere having an enhanced partial pressure of carbon dioxide relative to air. In a preferred embodiment, the atmosphere over the suspension has a partial pressure of carbon dioxide of at least 0.9; more preferably, at least about 0.95.

Quiescent cells may be returned to an active state by separating the cells from the motility inhibitor and exposing them to air. In addition, the initiation of an active state may be further induced by the dilution of the cells in a physiological saline (Salisbury et al., 1963) or a buffer such as TCA buffer or PBS. Typically, at least about 20%, preferably at least about 50%, more preferably at least about 60%, still more preferably at least about 70%, even more preferably at least about 80%, even more preferably at least about 90%, still more preferably at least about 95%, and most preferably at least about 99% of the cells returned to an active state (i.e., reactivated cells) will have a path velocity, progressive velocity, or both, as measured by HTM-IVOS sperm analysis, that is at least about 50%, preferably at least about 60%, more preferably at least about 70%, still more preferably at least about 80%, even more preferably at least about 90%, even more preferably at least about 95%, and most preferably at least about 99% of the path velocity, progressive velocity, or both of the sperm cells prior to being combined with the motility inhibitor (i.e., of sperm cells of a fresh ejaculate).

In general, the cell sorting process comprises a series of discrete steps, i.e., collection of a cell sample, staining of the cells, sorting of the cells, collection of the sorted cells, and optionally, cryoextension of the sorted cells. Advantageously, the motility inhibitor may be included in sperm suspensions formed or employed in one or more of these steps.

Collection of the Cell Sample

Intact viable bovine, porcine, equine, or other mammalian sperm cells, may be collected and contacted with the motility inhibitor. Various methods of collection of viable sperm are known and include, for example, the gloved-hand method, use of an artificial vagina, and electro-ejaculation. As an example, a bovine semen sample, typically containing about 0.5 to about 10 billion sperm cells per milliliter, may be collected directly from the source mammal into a vessel containing a motility inhibitor to form a sperm suspension. Alternatively, the semen sample may be collected into an empty vessel and then subsequently contacted with the motility inhibitor within several minutes to hours after collection to form the sperm suspension.

In addition to a buffer, the sperm suspension may also contain a range of additives to enhance sperm viability. Exemplary additives include protein sources, antibiotics, and compositions which regulate oxidation/reduction reactions intracellularly and/or extracellularly.

Exemplary protein sources include egg yolk, egg yolk extract, milk (including heat homogenized and skim), milk extract, soy protein, soy protein extract, serum albumin, bovine serum albumin, human serum substitute supplement, and combinations thereof. Albumin, and more particularly bovine serum albumin (BSA), is a preferred protein source. For example, if included, BSA may be present in the sperm suspension in an amount of less than about 5.0% (w/v), preferably less than about 2% (w/v), more preferably less than about 1% (w/v), and most preferably in an amount of about 0.1% (w/v).

The use of a protein source, such BSA, alone may initiate the process of capacitation in a percentage of the sperm cells in the suspension. It is preferred that this process take place in the female reproductive tract. Therefore, in order to inhibit the initiation of capacitation during dilution, as well as during the subsequent staining and sorting, an alternative protein source or a protein substitute may be included in the sperm suspension. The alternative protein source or protein substitute possess the advantageous effects of a typical protein source, such as BSA, in addition to the ability to inhibit the initiation of capacitation in a larger percentage of the cells in the sperm suspension. Examples of a alternative protein sources includes human serum substitute supplement (SSS)(Irvine Scientific, Santa Ana, Calif.) and cholesterol enhanced BSA, while an example of a protein substitute includes a polyvinyl alcohol, such as for example, a low to medium viscosity polyvinyl alcohol generally of a molecular weight of about 30,000 to about 60,000. Generally, if included, these compositions will be present in the same amounts as disclosed above with respect to BSA, with the total albumin content of the buffer or buffered solution generally not exceeding about 5.0% (w/v).

Exemplary compositions which regulates oxidation/reduction reactions intracellularly and/or extracellularly include for example pyruvate, vitamin K, lipoic acid, glutathione, flavins, quinones, superoxide dismutase (SOD), and SOD mimics. If included in the sperm suspension, such a composition may be present in a concentration sufficient to effect the protective effect without detrimentally affecting sperm health. Exemplary concentration ranges include from about 10 µM to about 20 mM depending upon such factors as the particular composition being used or the concentration of sperm in the suspension. For example, pyruvate may be present in the sperm suspension in a concentration from about 1 mM to about 20 mM, preferably from about 5 mM to about 15 mM, and more preferably about 10 mM. Vitamin K may be present in the sperm suspension in a concentration from about 1 µM to about 100 µM, preferably from about 10 µM to about 100 µM, and more preferably about 100 µM. Lipoic acid may be present in the sperm suspension in a concentration from about 0.1 mM to about 1 mM, preferably from about 0.5 mM to about 1 mM, and more preferably about 1 mM.

An antibiotic may be included in the sperm suspension in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, or any combination thereof. If included, the antibiotics may be present in a concentration of about 50 µg to about 800 µg per ml of semen, regardless of whether the semen is neat, buffered, or contains additional substances, such as for example, any of the additives mentioned herein. The Certified Semen Services (CSS) and National Association of Animal Breeders (NAAB) have promulgated guidelines regarding the use of antibiotics with respect to sperm collection and use.

A growth factor may be added to the sperm dispersion in order to help maintain the viability of the sperm cells. Exemplary growth factors include, for example, transforming growth factors ("TGF), such as, for example, TGFβ-1 and TGFβ-2, and insulin-like growth factors ("IGF"), such as for example, IGF-1. Generally, TGF may be present in the sperm dispersion in the form of TGFβ-1 in a concentration of about 0.1 ng/L to about 10 µg/L or as TGFβ-2 in a concentration of about 0.1 ng/L to about 200 ng/L, and IGF may be present in the sperm dispersion in the form of IGF-1 in a concentration of about 0.1 ng/L to about 50 µg/L. The use of such growth factors is well known in the art and is disclosed, for example, in U.S. Patent Application Publication No. 2003/0157473, the content of which is hereby incorporated herein by reference.

Once collected, the cells may be stored in a quiescent state for several hours at room temperature, for several weeks at a reduced temperature, such as for example at 5° C., or stored for several months in a cryoextender as discussed below. Preferably, the atmosphere above the cells has a high partial pressure of $CO_2$ as discussed above. Alternatively, the collected cells may be used within several hours, such as for example in a fertilization process, a staining process, or a sorting process.

Staining of the Cells

A motility inhibitor may be used to render cells immotile during staining of the cells. A process of staining sperm cells typically comprises the formation of a staining mixture, sometimes referred to as a labeling mixture, containing intact viable sperm cells, a motility inhibitor, and a dye, sometimes referred to as a label. In this aspect of the invention, the motility inhibitor may be contacted with the sperm cells to form a sperm suspension, and then the suspension contacted with a DNA selective dye. In this embodiment, the sperm source may be neat semen, or alternatively, a sperm-containing semen derivative obtained by centrifugation or the use of other means to separate semen into fractions.

In an alternative embodiment, the dye may be combined with a motility inhibitor, thereby forming a dye solution. Thus, for example, dye in the form of a neat solid, including a free-flowing powder, or a liquid composition may be combined with the inhibitor to form a dye solution, which may then be combined with neat semen, a sperm suspension, or a sperm-containing semen derivative.

In any event, the sperm cells will generally remain quiescent as long as they are maintained in the inhibitor. (Salisbury et al., 1963) Preferably, however, the staining mixture is maintained under an atmosphere having an enriched partial pressure of carbon dioxide relative to air; for example, providing an atmosphere over the staining mixture which is 99%+ $CO_2$ is generally preferred.

The pH of the staining mixture may be maintained at any of a range of pH's; typically this will be in the range of about 5.0 to about 9.0. For example, the staining mixture may be maintained at a "slightly acid" pH, i.e., from about 5.0 to about 7.0. In this embodiment, the pH is preferably from about 6.0 to about 7.0, more preferably from about 6.0 to about 6.5, and most preferably at about 6.2. Alternatively, the staining mixture may be maintained at a "slightly basic" pH, i.e., from about 7.0 to about 9.0. In this embodiment, the pH is preferably from about 7.0 to about 8.0, more preferably from about 7.0 to about 7.5, and most preferably at about 7.3.

The staining mixture may be formed by using one or more UV or visible light excitable, DNA selective dyes as previously described in U.S. Pat. No. 5,135,759 and WO 02/41906. Exemplary UV light excitable, selective dyes include Hoechst 33342 and Hoechst 33258, each of which is commercially available from Sigma-Aldrich (St. Louis, Mo.). Exemplary visible light excitable dyes include SYBR-14, commercially available from Molecular Probes, Inc. (Eugene, Oreg.) and bisbenzimide-BODIPY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino] propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm cells to an unacceptable degree when used in concentrations which enable sorting as described elsewhere.

Alternatively, the staining mixture may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., *Proc. Natl. Acad. Sci. USA,* 100(21): 12063-12068 (2003); Gygi, et al., *Nucleic Acids Res.,* 30(13): 2790-2799 (2002); U.S. Pat. No. 5,998,140; U.S. Pat. No. 6,143,901; and U.S. Pat. No. 6,090,947, the content of each of which is hereby incorporated herein by reference.

Fluorescent nucleotide sequences may also be used to label the sperm cells. Such nucleotide sequences fluoresce when hybridized to a nucleic acid containing a target or complementary sequence, but are otherwise non-fluorescent when in a non-hybridized state. Such oligonucleotides are disclosed, for example, in U.S. Patent Application Publication No. 2003/0113765 (hereby incorporated herein by reference).

Sex specific antibodies may also be used to label the sperm cells in a staining mixture. In this embodiment, for example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the non-fluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

Luminescent, color-selective nanocrystals may also be used to label sperm cells in a staining mixture. Also referred to as quantum dots, these particles are well known in the art, as demonstrated by U.S. Pat. No. 6,322,901 and U.S. Pat. No. 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207,392 and 6,247,323, each of which is hereby incorporated herein by reference).

The preferred concentration of the DNA selective or of any other type of dye in the staining mixture is a function of a range of variables which include the permeability of the cells to the selected dye, the temperature of the staining mixture, the amount of time allowed for staining to occur, and the degree of enrichment desired in the subsequent sorting step. In general, the dye concentration is preferably sufficient to achieve the desired degree of staining in a reasonably short period of time without substantially detrimentally affecting sperm viability. For example, the concentration of Hoechst 33342, Hoechst 33258, SYBR-14, or BBC in the staining mixture will generally be between about 0.1 μM and about 1.0M, preferably from about 0.1 μM to about 700 μM, and more preferably from about 100 μM to about 200 μM. In a particularly preferred embodiment, the concentration of Hoechst 33342, Hoechst 33258, SYBR-14, or BBC in the staining mixture will generally be between about 400 μM to about 500 μM, and most preferably about 450 μM. Accordingly, under one set of staining conditions, the concentration of Hoechst 33342 is preferably about 100 μM. Under another set of staining conditions, the concentration of Hoechst 33342 is about 150 μM. Under still another set of staining conditions the concentration is preferably about 200 μM. Under yet another set of staining conditions the concentration of Hoechst 33342 is most preferably about 450 μM.

As another example, the concentration of a fluorescent polyamide, such as for example, those described in U.S. Application Publication No. 2001/0002314, will generally be between about 0.1 μM and about 1 mM, preferably from about 1 μM to about 1 mM, more preferably about 5 μM to about 100 μM, even more preferably about 10 μM.

Optionally, the staining mixture may also contain additives to enhance sperm viability. Exemplary additives include an antibiotic, a growth factor or a composition which regulates oxidation/reduction reactions intracellularly and/or extracellularly as discussed above with respect to cell sample collection. These additives may be added to the collection fluid in accordance therewith.

Once formed, the staining mixture may be maintained at any of a range of temperatures; typically, this will be within a range of about 4° C. to about 50° C. For example, the staining mixture may be maintained at a "relatively low" temperature, i.e., a temperature of about 4° C. to about 30° C.; in this embodiment, the temperature is preferably from about 20° C. to about 30° C., more preferably from about 25° C. to about 30° C., and most preferable at about 28° C. Alternatively, the staining mixture may be maintained within an "intermediate" temperature range, i.e., a temperature of about 30° C. to about 39° C.; in this embodiment, the temperature is preferably at about 34° C. to about 39° C., and more preferably about 37° C. In addition, the staining mixture may be maintained within a "relatively high" temperature range, i.e., a temperature of about 40° C. to about 50° C.; in this embodiment, the temperature is preferably from about 40° C. to about 45° C., more preferably from about 40° C. to about 43° C., and most preferably at about 41° C. Selection of a preferred temperature generally depends upon a range of variables, including for example, the permeability of the cells to the dye(s) being used, the concentration of the dye(s) in the staining mixture, the amount of time the cells will be maintained in the staining mixture, and the degree of enrichment desired in the sorting step.

Uptake of dye by the sperm cells in the staining mixture is allowed to continue for a period of time sufficient to obtain the desired degree of DNA staining. That period is typically a period sufficient for the dye to bind to the DNA of the sperm cells such that X and Y chromosome-bearing sperm cells may be sorted based upon the differing and measurable fluorescence intensity between the two. Generally, this will be no more than about 160 minutes, preferably no more than about 90 minutes, still more preferably no more than about 60 minutes, and most preferably from about 5 minutes to about 40 minutes.

Accordingly, in one embodiment, a staining mixture is formed comprising sperm cells, a motility inhibitor, and a dye in a concentration from about 100 μM to about 200 μM, and the staining mixture is held for a period of time at a temperature of about 41° C. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In another embodiment, a staining mixture is formed comprising sperm cells, a motility inhibitor, and a dye in a concentration of about 400 μM to about 500 μM, and the staining mixture is held for a period of time at a temperature of about 41° C. In another embodiment, the dye concentration is 450 μM. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In still another embodiment, a staining mixture is formed comprising sperm cells, a motility inhibitor, and a dye in a concentration from about 100 μM to about 200 μM, and the staining mixture is held for a period of time at a temperature of about 28° C. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In yet another embodiment, a staining mixture is formed comprising sperm cells, a motility inhibitor, and a dye in a concentration from about 400 μM to about 500 μM, and the staining mixture is held for a period of time at a temperature of about 28° C. In another embodiment, the dye concentration is 450 μM. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

Sorting

A motility inhibitor may also be used to render the sperm cells immotile during sorting of the sperm cells. Generally, once the sperm are stained according to the present invention, they may be sorted according to any known means that allows for separation based upon fluorescence. Commonly used and well known methods include flow cytometry systems, as exemplified by and described in U.S. Pat. Nos. 5,135,759, 5,985,216, 6,071,689, 6,149,867, and 6,263,745, International Patent Publications WO 99/33956 and WO 01/37655, and U.S. patent application Ser. No. 10/812,351, the content of which is hereby incorporated herein by reference, and corresponding International Patent Publication WO 2004/088283. When sorting according to such methods, the sperm are introduced into the nozzle of a flow cytometer in a sample fluid. In one embodiment, therefore, the sample fluid may comprise the stained sperm cells and a motility inhibitor.

Likewise, the sheath fluid used to surround the stream of sample fluid as it travels through the cytometer may also comprise a motility inhibitor. Generally, the sheath fluid may be introduced into a nozzle of the cytometer using pressurized gas or by a syringe pump. Preferably, the pressurized gas is carbon dioxide or nitrogen, more preferably nitrogen. Alternatively, the pressurized gas may be carbon dioxide, although under such circumstances, care may be taken to minimize effervescence.

Optionally, the sample fluid or sheath fluid may also contain additive, such as, an antibiotic, a growth factor or a composition which regulates oxidation/reduction reactions intracellularly or extracellularly as discussed above with respect to cell sample collection Each of these additives may be added to either fluid in accordance therewith.

Collection of the Sorted Cells

Once sorted, the sorted cells are collected in a vessel that contains a collection fluid. Generally, the purpose of the collection fluid includes cushioning the impact of the sperm cells with the collection vessel or providing a fluid support for the cells.

In one embodiment, the collection fluid comprises a motility inhibitor and a protein source. If included, the protein source may be any protein source that does not interfere with the viability of the sperm cells and is compatible with the motility inhibitor. Examples of common protein sources include milk (including heat homogenized and skim), milk extract, egg yolk, egg yolk extract, soy protein and soy protein extract. Such proteins may be used in a concentration from about 1% (v/v) to about 30% (v/v), preferably from about 10% (v/v) to about 20% (v/v), and more preferably about 10% (v/v).

Optionally, the collection fluid may also contain additives such as, an antibiotic, a growth factor or a composition which regulates oxidation/reduction reactions intracellularly or extracellularly as discussed above with respect to cell sample collection. Each of these additives may be added to the collection fluid in accordance therewith.

Accordingly, in a certain embodiment, the collection fluid comprises 0.097 moles/L of $NaHCO_3$, 0.173 moles/L of $KHCO_3$, 0.090 moles/L $C_6H_8O_7.H_2O$ and 10% (v/v) egg yolk in water, at a pH of about 6.2, more preferably of about 7.0, and even more preferably of about 6.5. Preferably, the collection fluid is maintained under an atmosphere having an enriched partial pressure of carbon dioxide relative to air; for example, the atmosphere may have a partial pressure of carbon dioxide in excess of 0.9, more preferably 0.95 and still more preferably 0.99.

In lieu of the use of a more traditional collection fluid, the sorted cells may be collected into a vessel containing or coated with a cryoextender. Accordingly, in one particular embodiment, the sorted cells are collected into a cryoextender comprising a motility inhibitor. In another embodiment, the sorted cells are collected into a cryoextender comprising a motility inhibitor, water, Triladyle (Minitube, Verona, Wis., comprising glycerol, tris, citric acid, fructose, 5 mg/100 ml tylosin, 25 mg/100 ml gentamycin, 30 mg/100 ml Spectinomycin, and 15 mg/100 ml Lincomycin), egg yolk, and pyruvic acid. In yet another embodiment, the collection fluid is the cryoextender comprising 0.097 moles/L of $NaHCO_3$, 0.173 moles/L of $KHCO_3$, 0.090 moles/L $C_6H_8O_7.H_2O$ in water, and 25 g Triladyl®, 25 g egg yolk, and 10 mM pyruvic acid per 75 mL of water.

Cryoextension of the Sorted Cells

Once the sperm have been sorted and collected into collection vessels, they may be used for inseminating female mammals. This can occur almost immediately, requiring little additional treatment of the sperm. Likewise, the sperm may also be cooled or frozen for use at a later date. In such instances, the sperm may benefit from the addition of a cryoextender to minimize the impact upon viability or post-thaw motility as a result of cooling and freezing.

A motility inhibitor may be used to render cells in the cryoextender immotile. Generally, a cryoextender may comprise a motility inhibitor, a protein source, and a cryoprotectant. If included, a protein source may be added to provide support to the cells and to cushion the contact of the cells with the collection vessel. The protein source may be any protein source that does not interfere with the viability of the sperm cells and is compatible with the motility inhibitor. Examples of common protein sources include milk (including heat homogenized and skim), milk extract, egg yolk, egg yolk extract, soy protein and soy protein extract. Such proteins may be found in a concentration from about 10% (v/v) to about 30% (v/v), preferably from about 10% (v/v) to about 20% (v/v), and more preferably about 20% (v/v).

A cryoprotectant is preferably included in the cryoextender to lessen or prevent cold shock or to maintain fertility of the sperm. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl®, and combinations thereof. If included, generally, these cryoprotectants are present in the cryoextender in an amount of about 1% (v/v) to about 15% (v/v), preferably in an amount of about 5% (v/v) to about 10% (v/v), more preferably in an amount of about 7% (v/v), and most preferably in an amount of about 6% (v/v).

In one particular embodiment, the cryoextender comprises a motility inhibitor, water, Triladyl®, egg yolk, and pyruvic acid. In yet another embodiment, the cryoextender comprises 0.097 moles/L of $NaHCO_3$, 0.173 moles/L of $KHCO_3$, 0.090 moles/L $C_6H_8O_7.H_2O$ in water, and 25 g Triladyl®, 25 g egg yolk, and 10 mM pyruvic acid per 75 mL of water.

In another particular embodiment, the cryoextender comprises a motility inhibitor, water, Triladyl®, and egg yolk. In yet another embodiment, the cryoextender comprises 0.097 moles/L of $NaHCO_3$, 0.173 moles/L of $KHCO_3$, 0.090 moles/L $C_6H_8O_7 \cdot H_2O$ in water, and 25 g Triladyl®, and 25 g egg yolk per 75 mL of water.

Optionally, the cryoextender may also contain an antibiotic, a growth factor or a composition which regulates oxidation/reduction reactions intracellularly and/or extracellularly as discussed above with respect to cell sample collection Each of these additives may be added to the collection fluid in accordance therewith.

Having described the invention in detail, it will be apparent that modifications and variations are possible without departing the scope of the invention defined in the appended claims.

EXAMPLES

The following non-limiting examples are provided to further illustrate the present invention.

Example 1

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, several tubes of $150 \times 10^6$ sperm/ml suspensions were prepared by suspending semen in a TCA buffer or a carbonate-based inhibitor. Table I. below illustrates the compositions and staining conditions used.

TABLE I

| Sample Name | Composition | pH | Conc. (uM) Hoechst | Temperature (° C.) |
|---|---|---|---|---|
| 10 mM pyr TCA | 10 mM pyruvate in TCA | 7.3 | 600 μM | 28° C. |
| 10 mM pyr $CO_2$ | 10 mM pyruvate in TCA blanket with $CO_2$ balloon | 7.3 | 600 μM | 28° C. |
| Carbonate 6.2 | Carbonate based inhibitor, pH 6.2 | 6.2 | 600 μM | 28° C. |
| Carbonate 7.3 | Carbonate based inhibitor, pH 7.3 | 7.3 | 600 μM | 28° C. |

Figure 2:
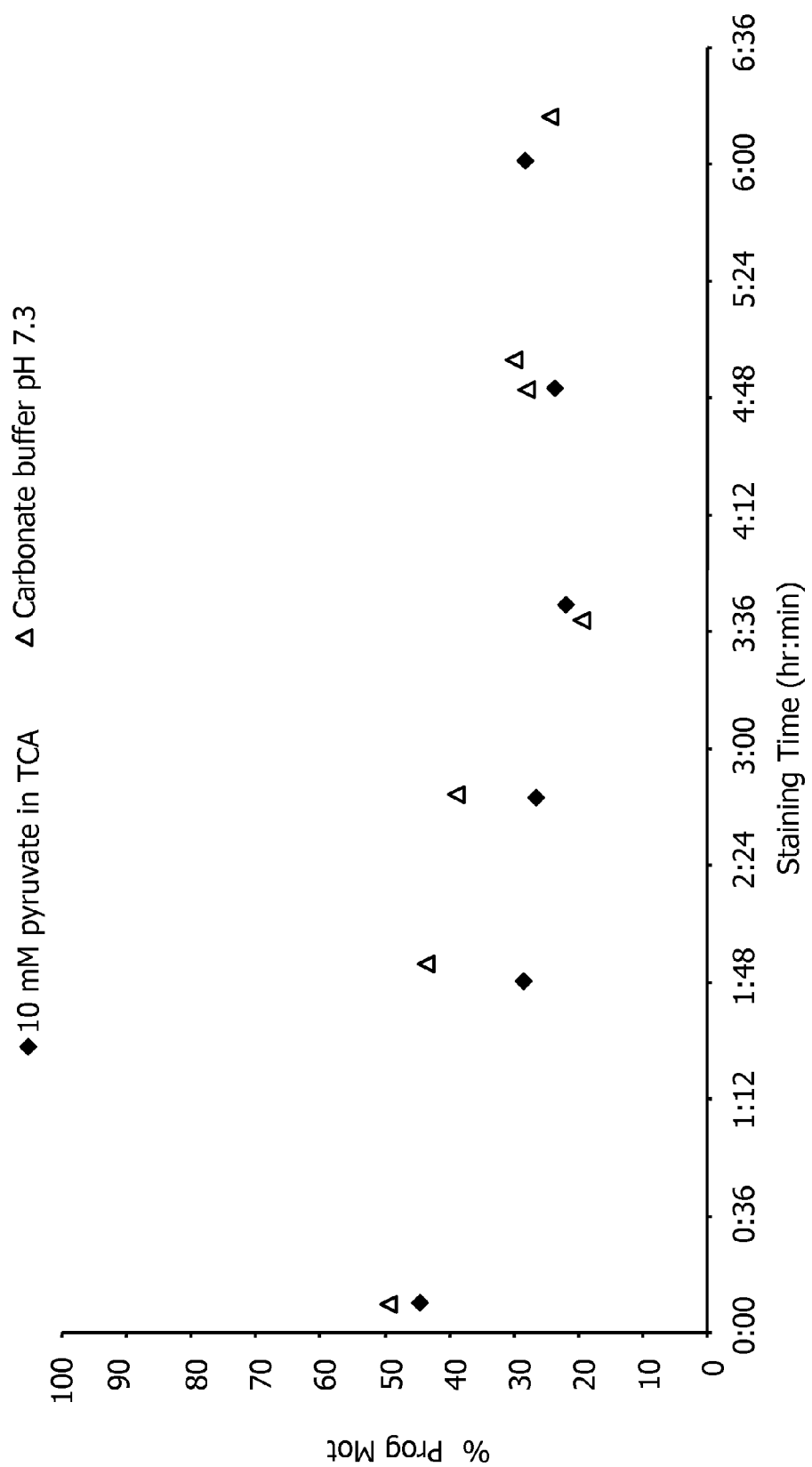
FIG. 2 graphically depicts the results of the study carried out in Example 1 wherein percent progressive motility of sperm cells is measured for sperm cells stained with 600 μM Hoechst 33342 dye at 28° C. in TCA containing 10 mM pyruvate or a carbonate-based inhibitor at pH 7.3.
Figure 3:
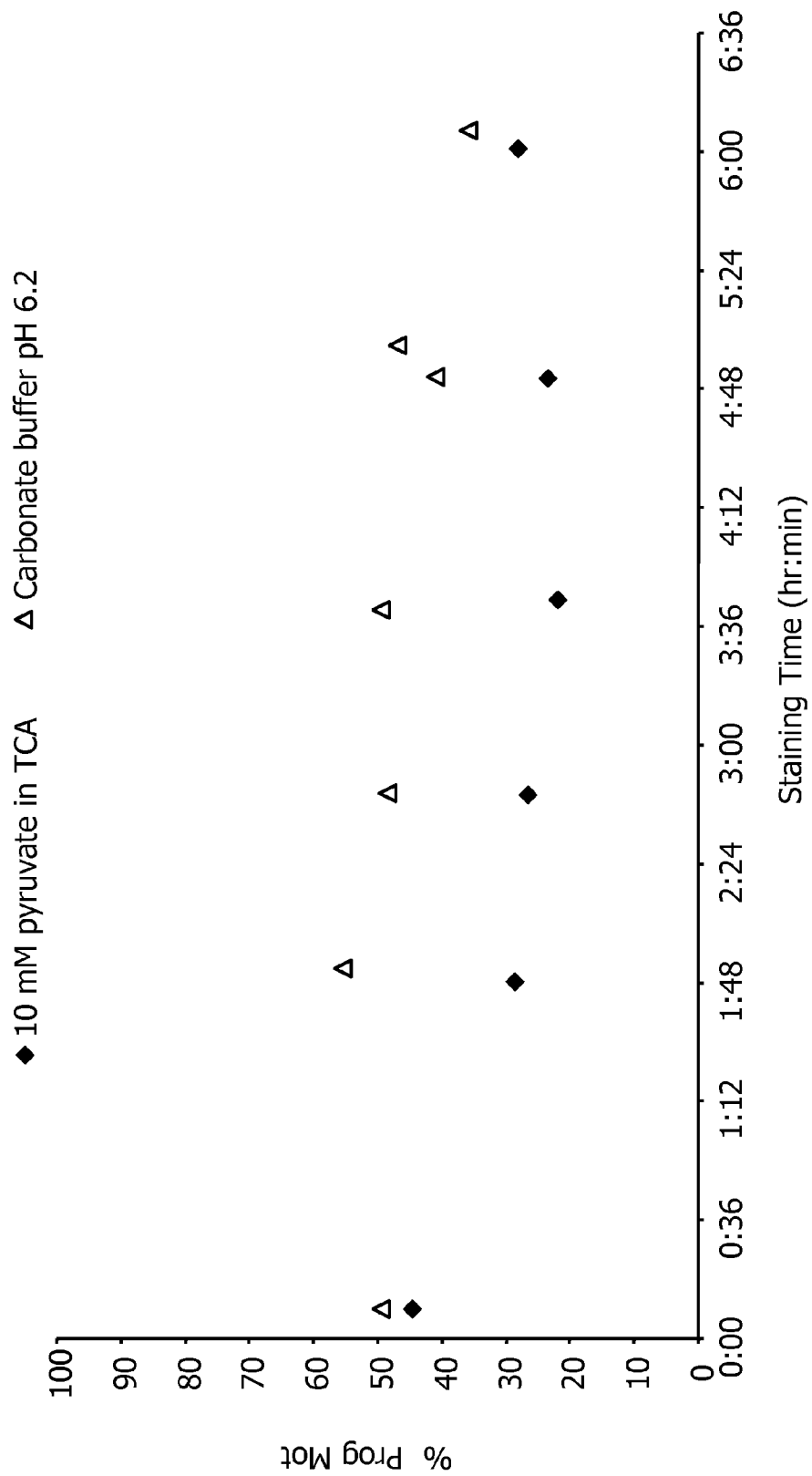
FIG. 3 graphically depicts the results of the study carried out in Example 1 wherein percent progressive motility of sperm cells is measured for sperm cells stained with 600 μM Hoechst 33342 dye at 28° C. in TCA containing 10 mM pyruvate or a carbonate-based inhibitor at pH 6.2.

To the sperm suspensions, aliquots of a 10 mM Hoechst solution in water were added to yield a concentration of 600 μM Hoechst. The sperm suspensions were maintained in a 28° C. water bath for the duration of the staining period (approximately 1 hour). Sperm suspensions were analyzed by removing a 50 μL aliquot from the stained sperm suspension, adding 200 μL of 25° C. 10 mM pyruvate in TCA at pH 7.3 to initiate the reversal of the quiescence, allowing at least a five minute equilibration period, and analyzing by IVOS to measure percent progressive motility (% Prog. Mot.). Comparisons of the IVOS percent progressive motilities are seen in FIGS. 1-3.

Example 2

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. Theriogenology, 49(4): 871-9 (March 1998)). Based on the semen concentration, several tubes of $450 \times 10^6$ sperm/ml suspensions were prepared by suspending semen in either a TCA buffer or a carbonate based inhibitor. Table II. below illustrates the compositions and staining conditions used.

TABLE II

| Sample Name | Composition | pH | Conc. (uM) Hoechst | Temperature (° C.) |
|---|---|---|---|---|
| 10 mM pyr TCA | 10 mM pyruvate in TCA | 7.3 | 1000 μM | 28° C. |
| Carbonate 6.2 | Carbonate based inhibitor, pH 6.2 | 6.2 | 1000 μM | 28° C. |
| Carbonate 7.3 | Carbonate based inhibitor, pH 7.3 | 7.3 | 1000 μM | 28° C. |

Figure 4:
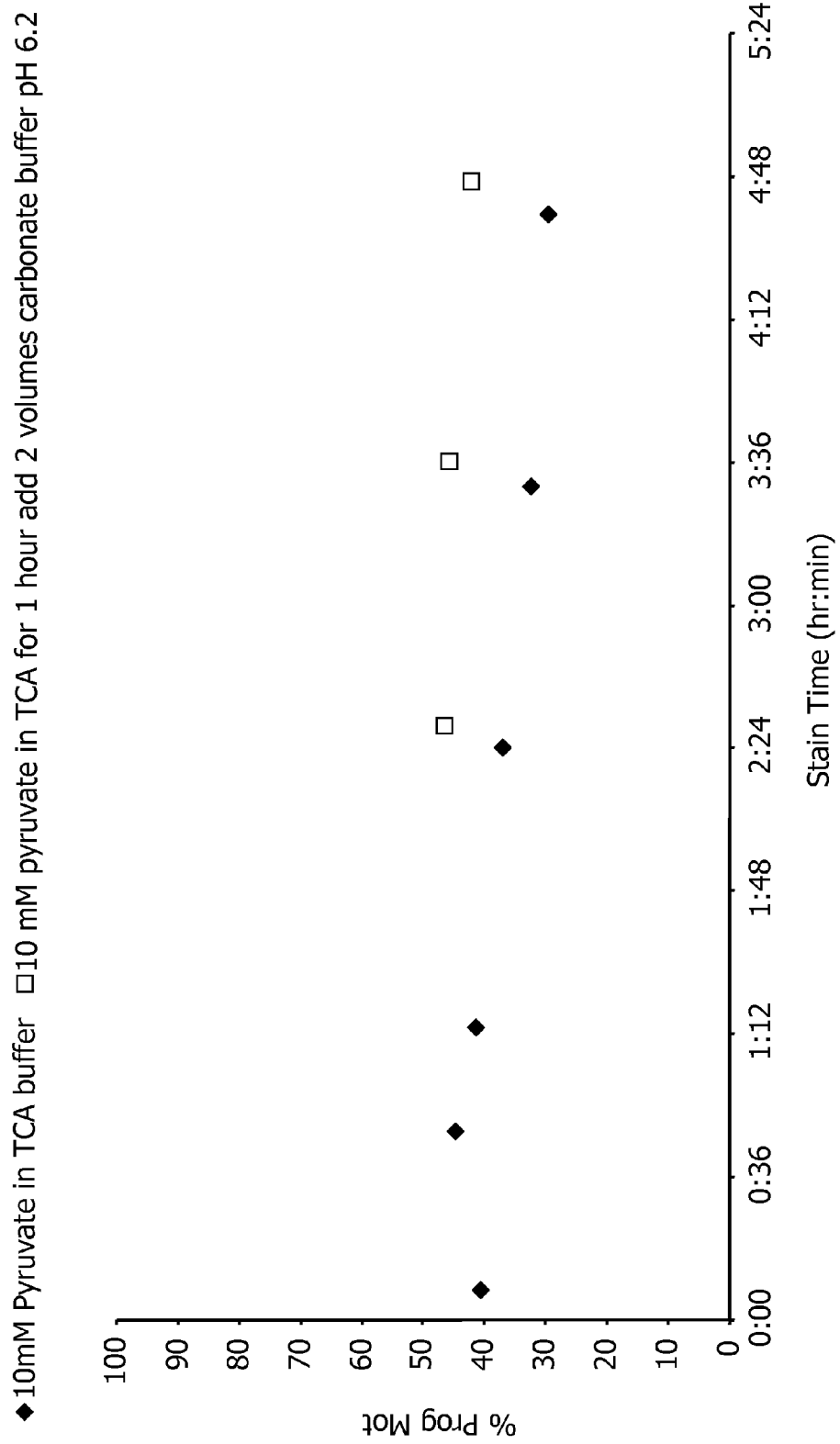
FIG. 4 graphically depicts the results of the study carried out in Example 2 wherein percent progressive motility of sperm cells is measured for sperm cells stained with 1000 μM Hoechst 33342 dye at 28° C. in TCA containing 10 mM pyruvate and then diluted 1 to 3 with either TCA containing 10 mM pyruvate or a carbonate-based inhibitor at pH 6.2.
Figure 5:
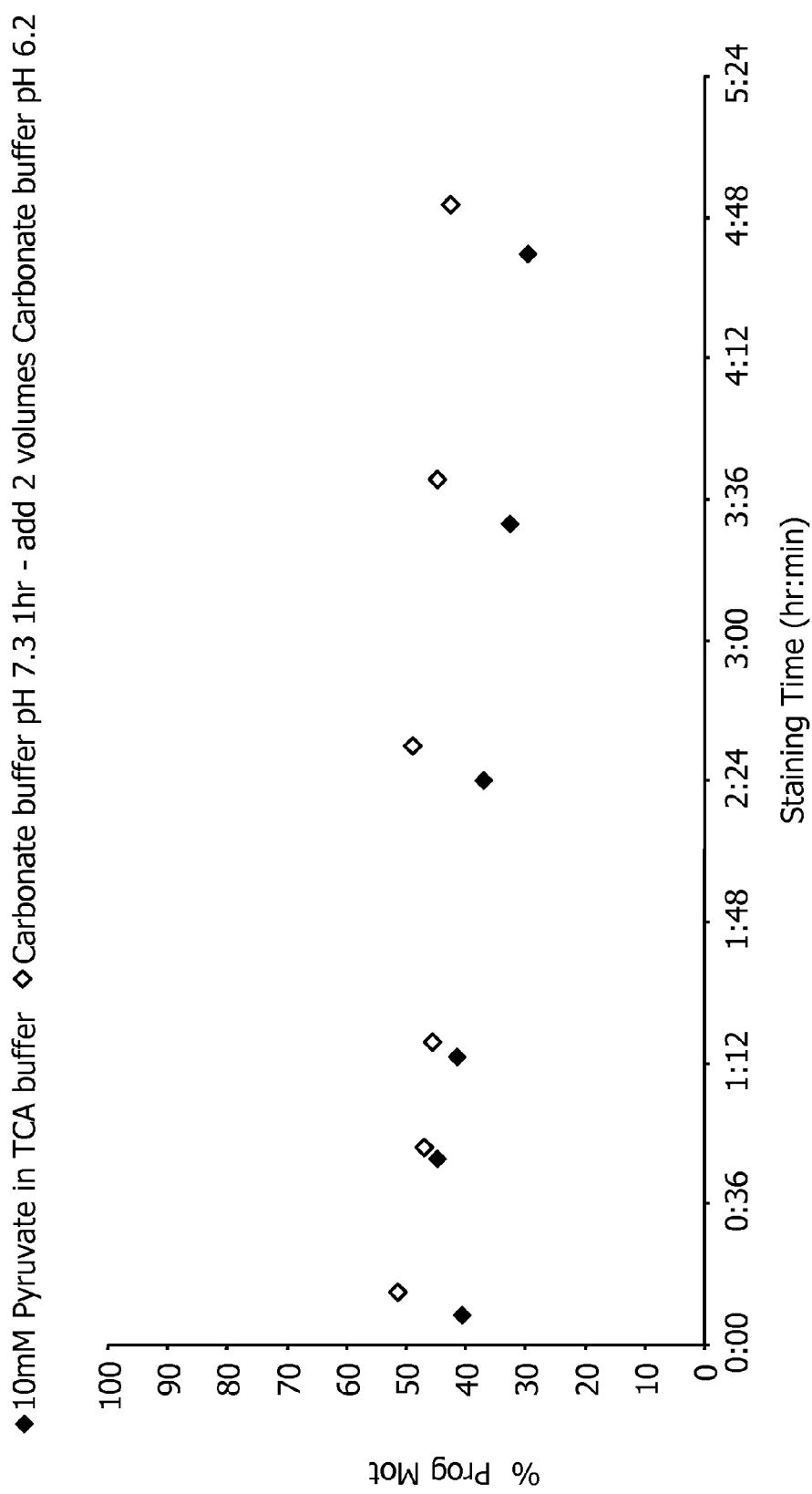
FIG. 5 graphically depicts the results of the study carried out in Example 2 wherein percent progressive motility of sperm cells is measured for sperm cells stained with 1000 μM Hoechst 33342 dye at 28° C. in (1) TCA containing 10 mM pyruvate and diluted 1 to 3 with the same or (2) a carbonate-based buffer at pH 7.3 and diluted 1 to 3 with carbonate-based inhibitor at pH 6.2.
Figure 6:
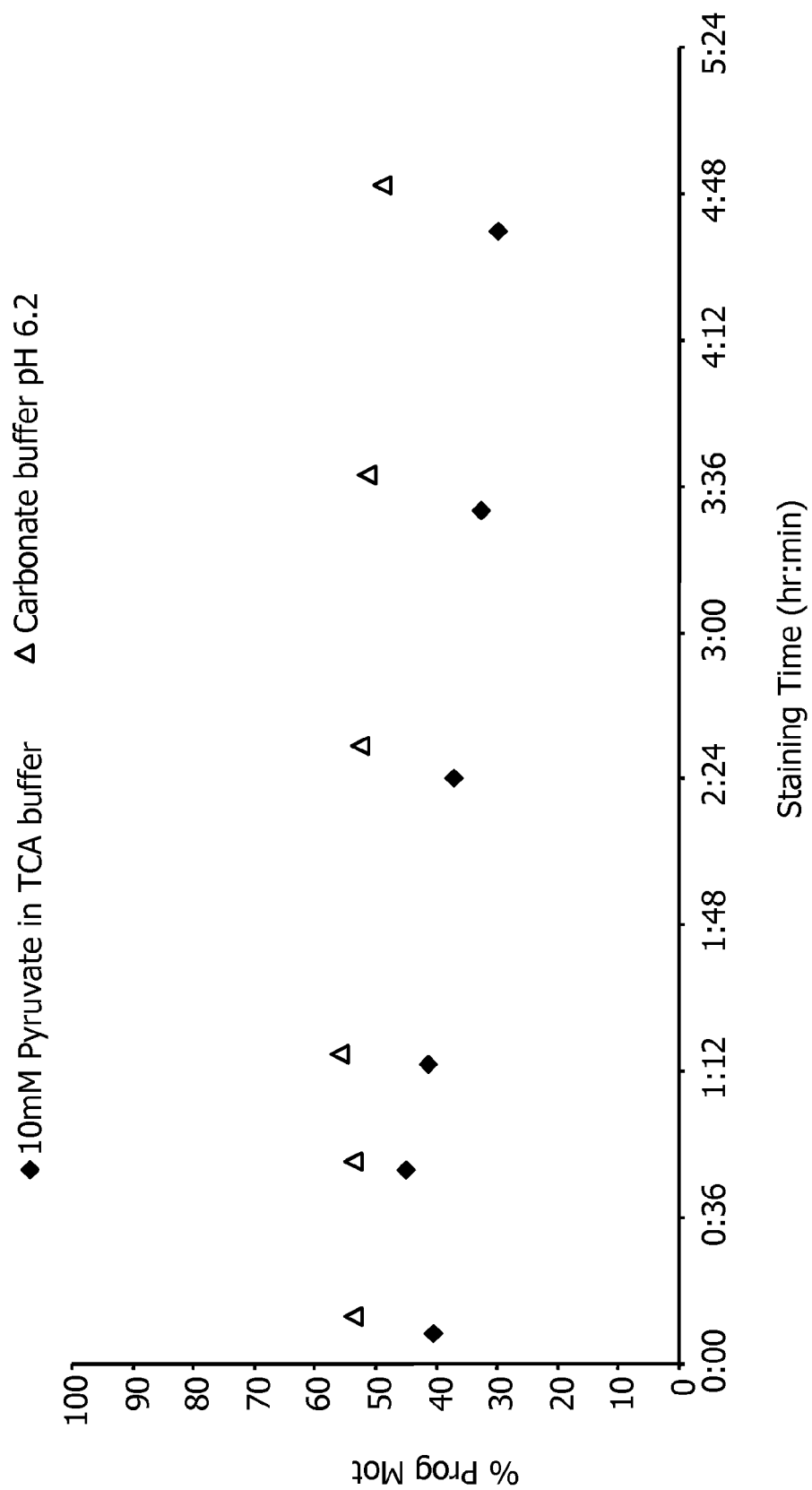
FIG. 6 graphically depicts the results of the study carried out in Example 2 wherein percent progressive motility of sperm cells is measured for sperm cells stained with 1000 μM Hoechst 33342 dye at 28° C. in TCA containing 10 mM pyruvate or a carbonate-based inhibitor at pH 6.2.

To the sperm suspensions, aliquots of a 10 mM Hoechst solution in water were added to yield a concentration of 1000 μM Hoechst. The sperm suspensions were maintained in a 28° C. water bath for 1 hour, and were then diluted to $150 \times 10^6$ sperm/ml with 10 mM pyruvate in TCA or a carbonate-based inhibitor at a pH 6.2 as specifically indicated in each figure to dilute to a concentration typical for sorting. Sperm suspensions were analyzed by removing a 50 μL aliquot from the stained and diluted sperm suspension at the time period designated within each figure and adding 200 μL of 25° C. 10 mM pyruvate in TCA at pH 7.3 to initiate the reversal of the quiescence, allowing at least a five minute equilibration period, and analyzing the aliquot by IVOS to measure the percent progressive motility. Comparisons of the IVOS percent progressive motilities are seen in FIGS. 4-6.

Example 3

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. Theriogenology, 49(4): 871-9 (March 1998)). Based on the semen concentration, several tubes of $450 \times 10^6$ sperm/ml suspensions were prepared by suspending semen in either a TCA buffer or a carbonate based inhibitor. Table III. below illustrates the compositions and staining conditions used.

TABLE III

| Sample Name | Buffer | pH | Conc (uM) Hoechst | Temperature (° C.) |
|---|---|---|---|---|
| 10 mM pyr TCA | 10 mM pyruvate in TCA | 7.3 | 300 μM | 41° C. |
| Carbonate 6.2 | Carbonate based inhibitor, pH 6.2 | 6.2 | 300 μM | 41° C. |
| Carbonate 7.3 | Carbonate based inhibitor, pH 7.3 | 7.3 | 300 μM | 41° C. |

Figure 7:
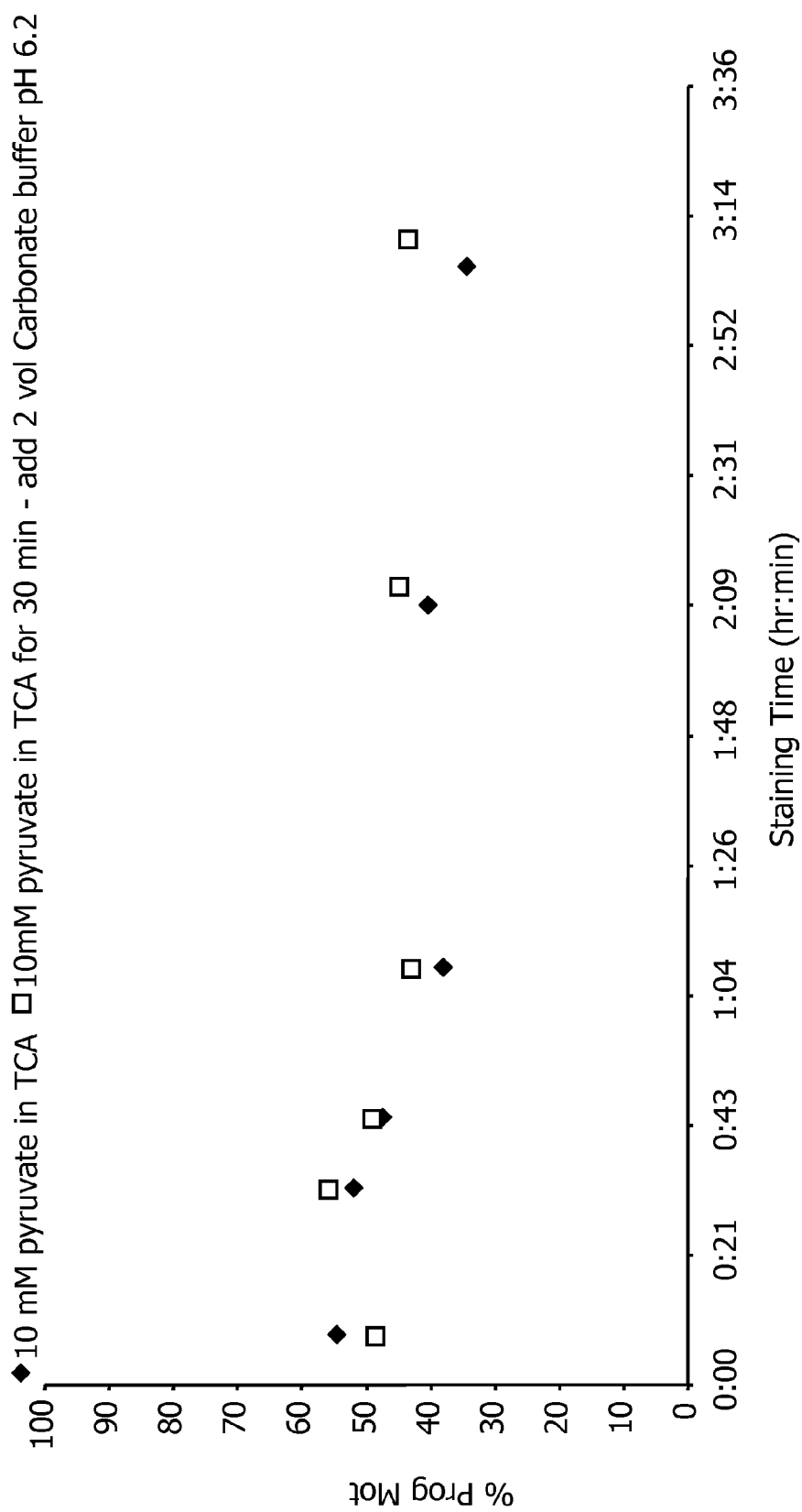
FIG. 7 graphically depicts the results of the study carried out in Example 3 wherein percent progressive motility of sperm cells is measured for sperm cells stained with 300 μM Hoechst 33342 dye at 41° C. in TCA containing 10 mM pyruvate and then diluted 1 to 3 with either TCA containing 10 mM pyruvate or a carbonate-based inhibitor at pH 6.2.
Figure 8:
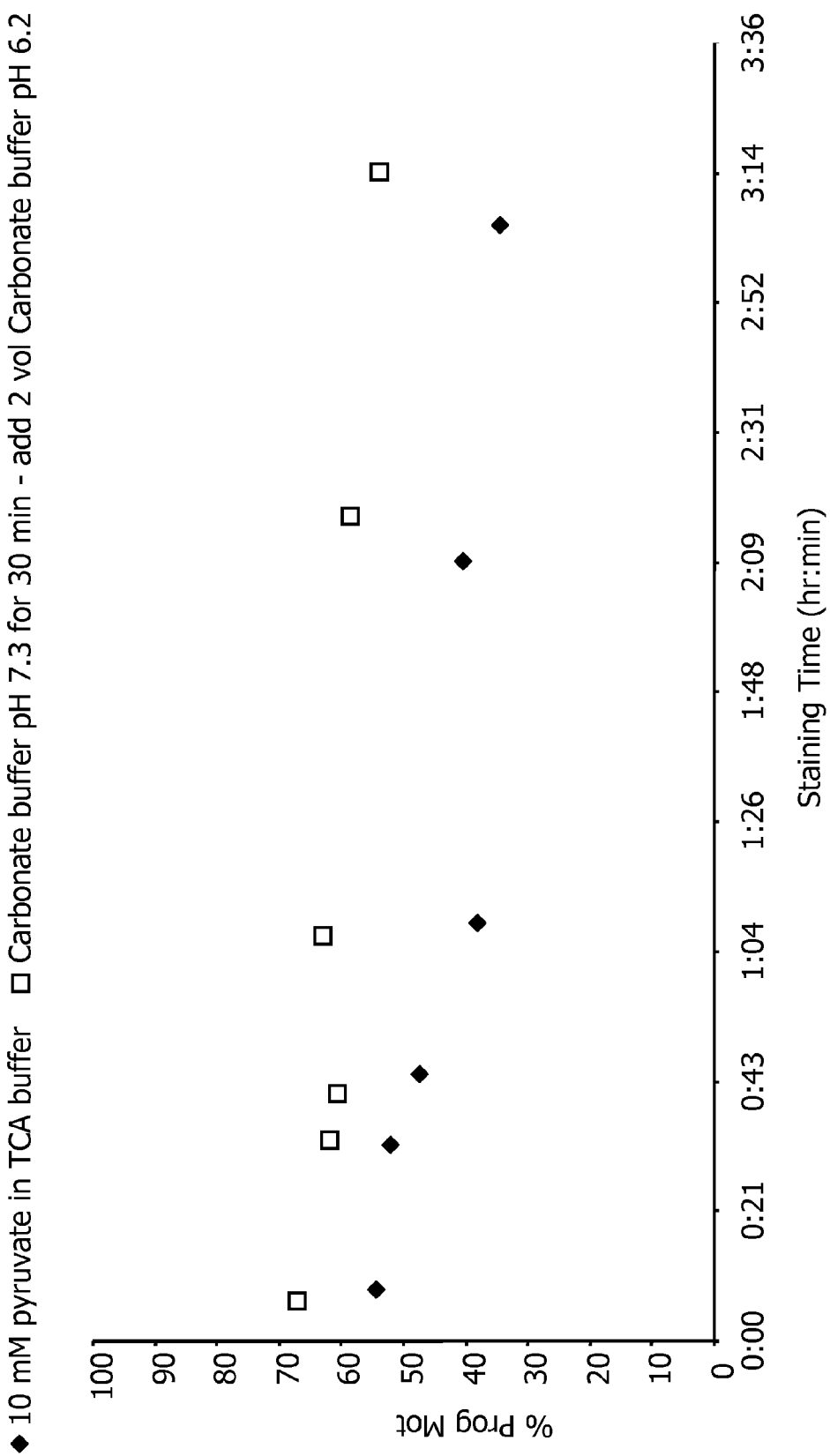
FIG. 8 graphically depicts the results of the study carried out in Example 3 wherein percent progressive motility of sperm cells is measured for sperm cells stained with 300 μM Hoechst 33342 dye at 41° C. in (1) TCA containing 10 mM pyruvate and diluted 1 to 3 with the same or (2) a carbonate-based buffer at pH 7.3 and diluted 1 to 3 with carbonate-based inhibitor at pH 6.2.
Figure 9:
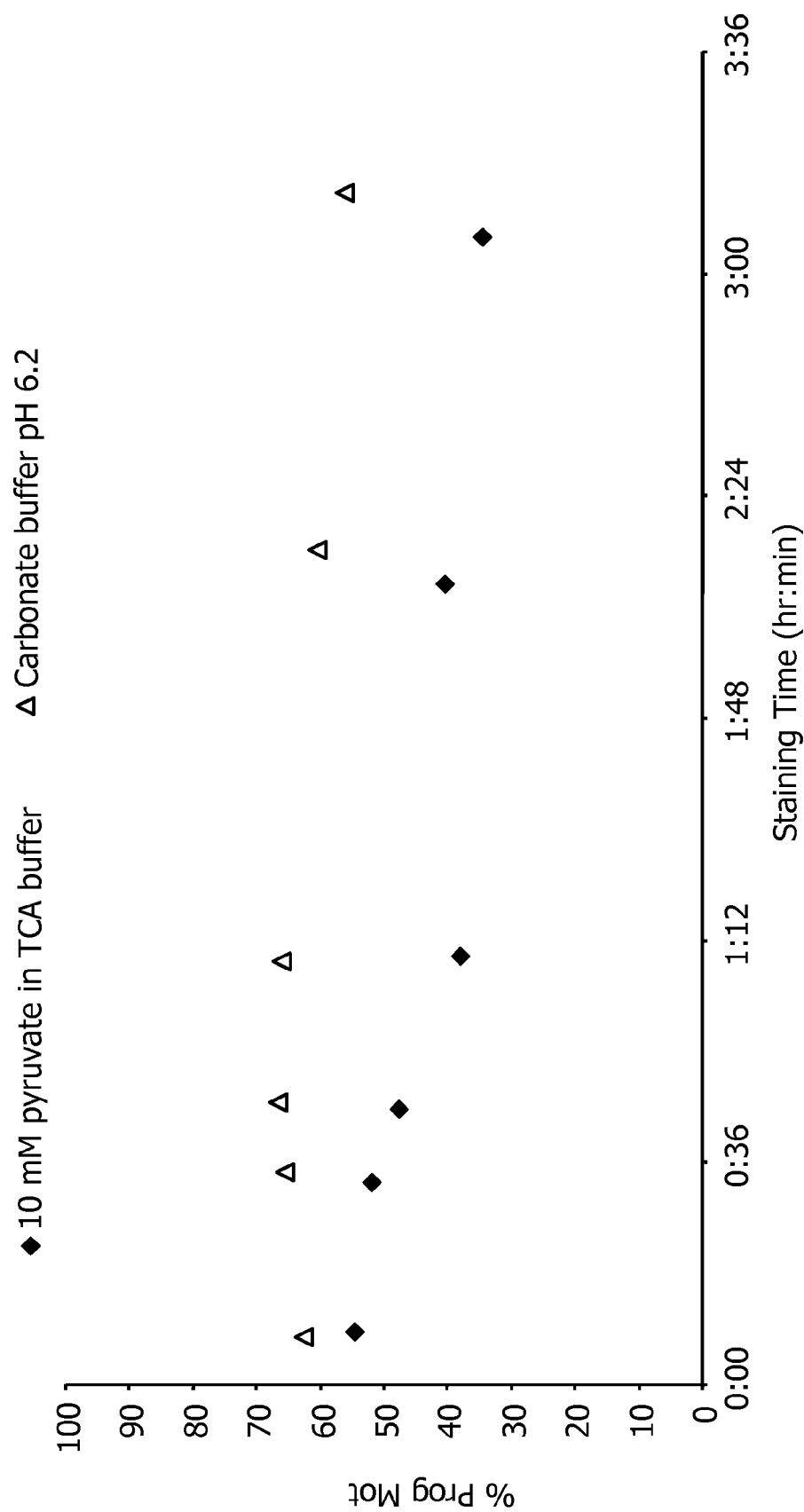
FIG. 9 graphically depicts the results of the study carried out in Example 3 wherein percent progressive motility of sperm cells is measured for sperm cells stained with 300 μM Hoechst 33342 dye at 41° C. in TCA containing 10 mM pyruvate or a carbonate-based inhibitor at pH 6.2.

To the sperm suspensions, aliquots of a 10 mM Hoechst solution in water were added to yield a concentration of 300 μM Hoechst. The sperm suspensions were maintained in a 41° C. water bath for 30 minutes, and then diluted to $150 \times 10^6$ sperm/ml with 10 mM pyruvate in TCA or a carbonate-based inhibitor at pH 6.2 as specifically indicated in each figure to dilute to a concentration typical for sorting. Sperm suspensions were analyzed by removing a 50 μL aliquot from the stained and diluted sperm suspension at the time period designated within each figure and adding 200 μL of 25° C. 10 mM pyruvate in TCA at pH 7.3 to initiate the reversal of the quiescence, allowing at least a five minute equilibration period, and analyzing by IVOS to measure the percent progressive motility. Comparisons of the IVOS percent progressive motilities are seen in FIGS. 7-9.

Example 4

Figure 10:
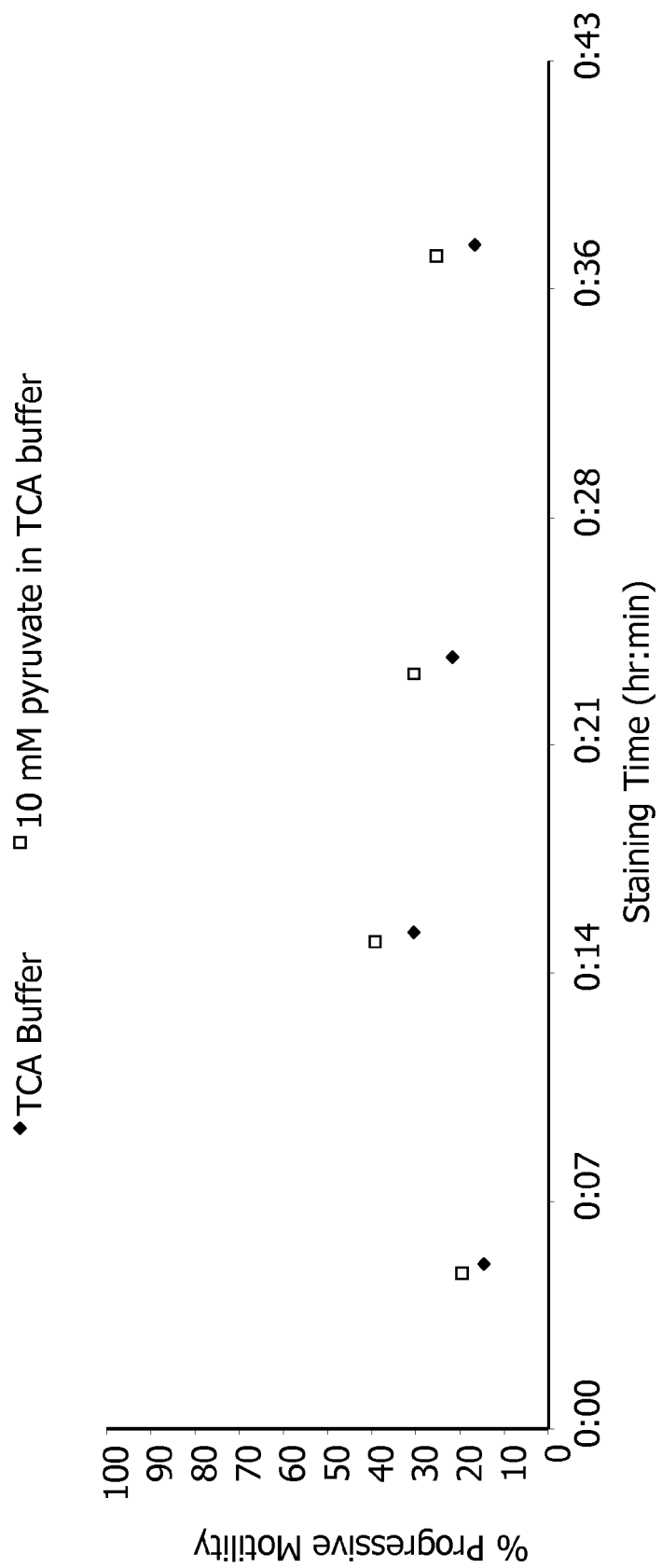
FIG. 10 graphically depicts the results of the study carried out in Example 4 wherein percent progressive motility of sperm is measured for sperm stained with 400 μM Hoechst 33342 dye at 41° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. Theriogenology, 49(4): 871-9 (March 1998)). Based on the semen concentration, 1 mL of $150 \times 10^6$ sperm/ml suspension was prepared by removing an aliquot of the carbonate sperm suspension centrifuging the sperm suspension at 500×g for 5 minutes, removing the supernatant and re-suspending the pellet in 41° C. TCA buffer pH 7.3. An additional 1 mL of $150 \times 10^6$ sperm/ml was prepared by suspending an aliquot of semen in 41° C. TCA buffer containing 10 mM pyruvate at pH 7.3. To the sperm suspensions, aliquots of a 10 mM Hoechst solution in water were added to yield the dye concentration of 400 μM Hoechst. The sperm suspensions were maintained in a 41° C. water bath for the duration of the staining period. Sperm suspensions were analyzed by removing a 50 μL aliquot from the staining sperm suspension, adding 200 μL of the same buffer at the same temperature and analyzing by IVOS to measure % progressive motility (% Prog Mot). Results of the IVOS analysis are summarized in FIG. 10.

Example 5

Figure 11:
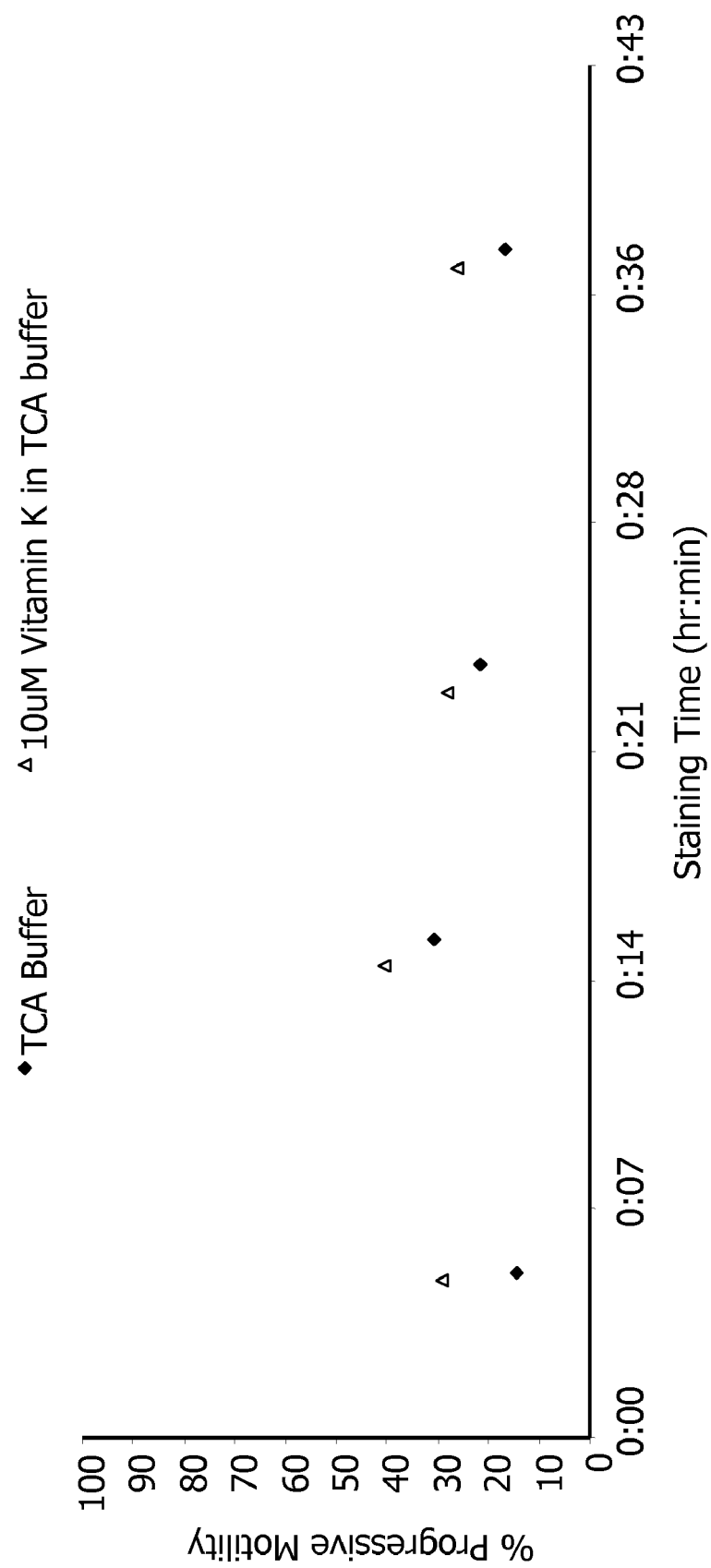
FIG. 11 graphically depicts the results of the study carried out in Example 5 wherein percent progressive motility of sperm is measured for sperm stained with 400 μM Hoechst 33342 dye at 41° C. in either a TCA buffer or a TCA buffer containing 10 μM vitamin K.

Sperm samples were obtained and prepared in the same manner as in Example 4 with the following exception. The buffer used to suspend the sperm for staining and IVOS analysis were TCA and TCA containing 10 uM Vitamin K. Results of the IVOS analysis are summarized in FIG. 11.

Example 6

Figure 12:
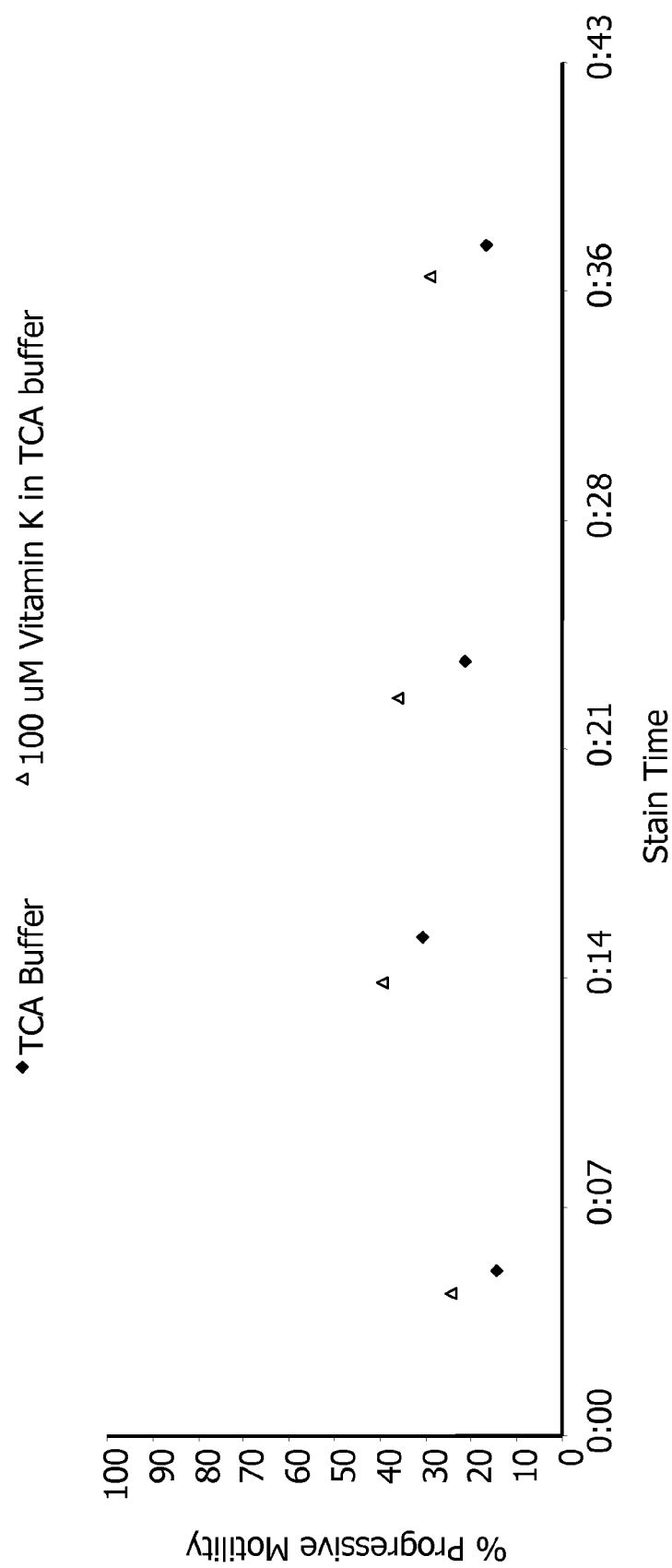
FIG. 12 graphically depicts the results of the study carried out in Example 6 wherein percent progressive motility of sperm is measured for sperm stained with 400 μM Hoechst 33342 dye at 41° C. in either a TCA buffer or a TCA buffer containing 100 μM vitamin K.

Sperm samples were obtained and prepared in the same manner as in Example 4 with the following exception. The buffer used to suspend the sperm for staining and IVOS analysis were TCA and TCA containing 100 uM Vitamin K. Results of the IVOS analysis are summarized in FIG. 12.

Example 7

Figure 13:
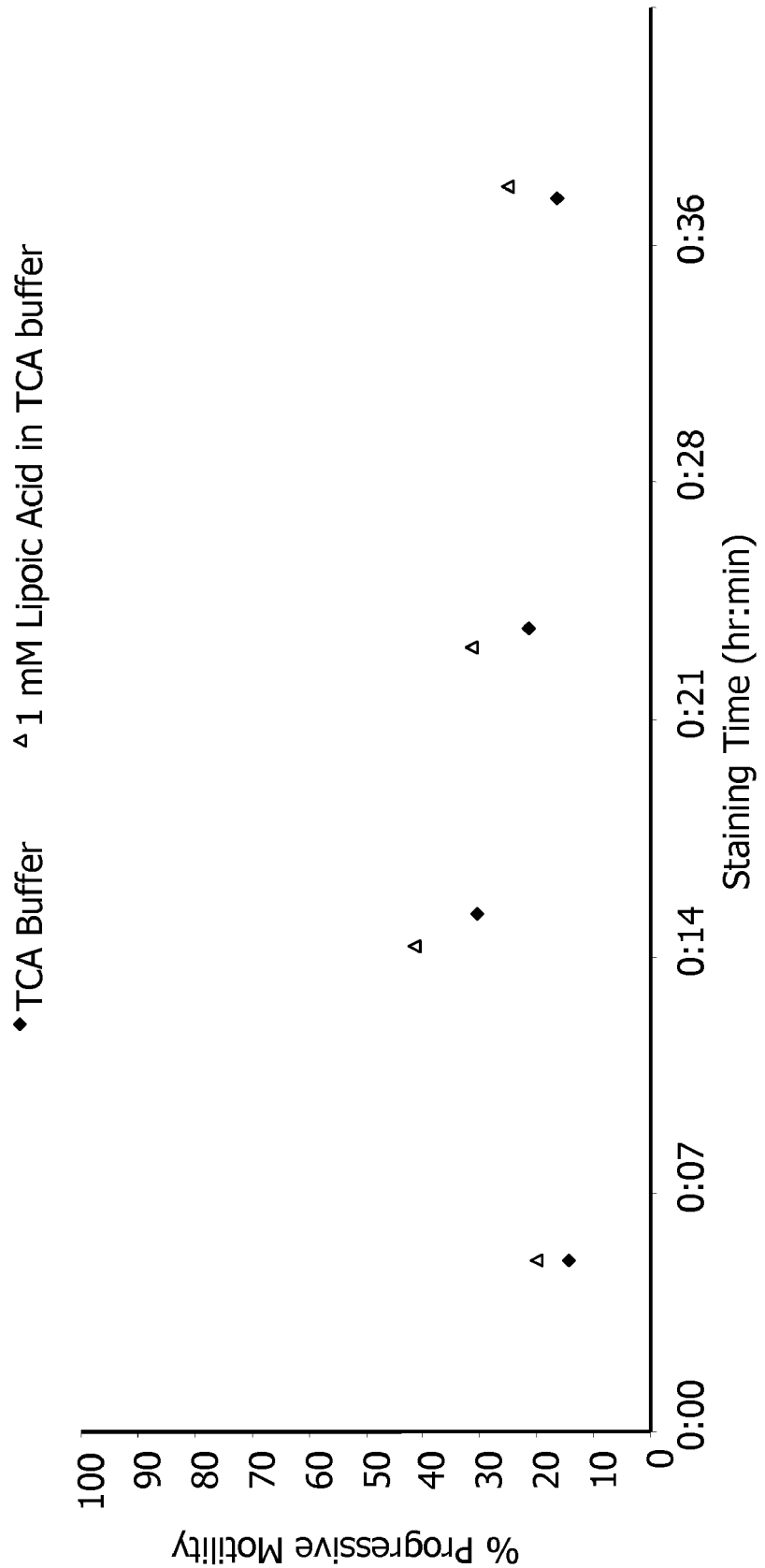
FIG. 13 graphically depicts the results of the study carried out in Example 7 wherein percent progressive motility of sperm is measured for sperm stained with 400 μM Hoechst 33342 dye at 41° C. in either a TCA buffer or a TCA buffer containing 1 mM lipoic acid.

Sperm samples were obtained and prepared in the same manner as in Example 4 with the following exception. The buffers used to suspend the sperm for staining and IVOS analysis were TCA and TCA containing 1 mM Lipoic Acid. Results of the IVOS analysis are summarized in FIG. 13.

Example 8

Figure 14:
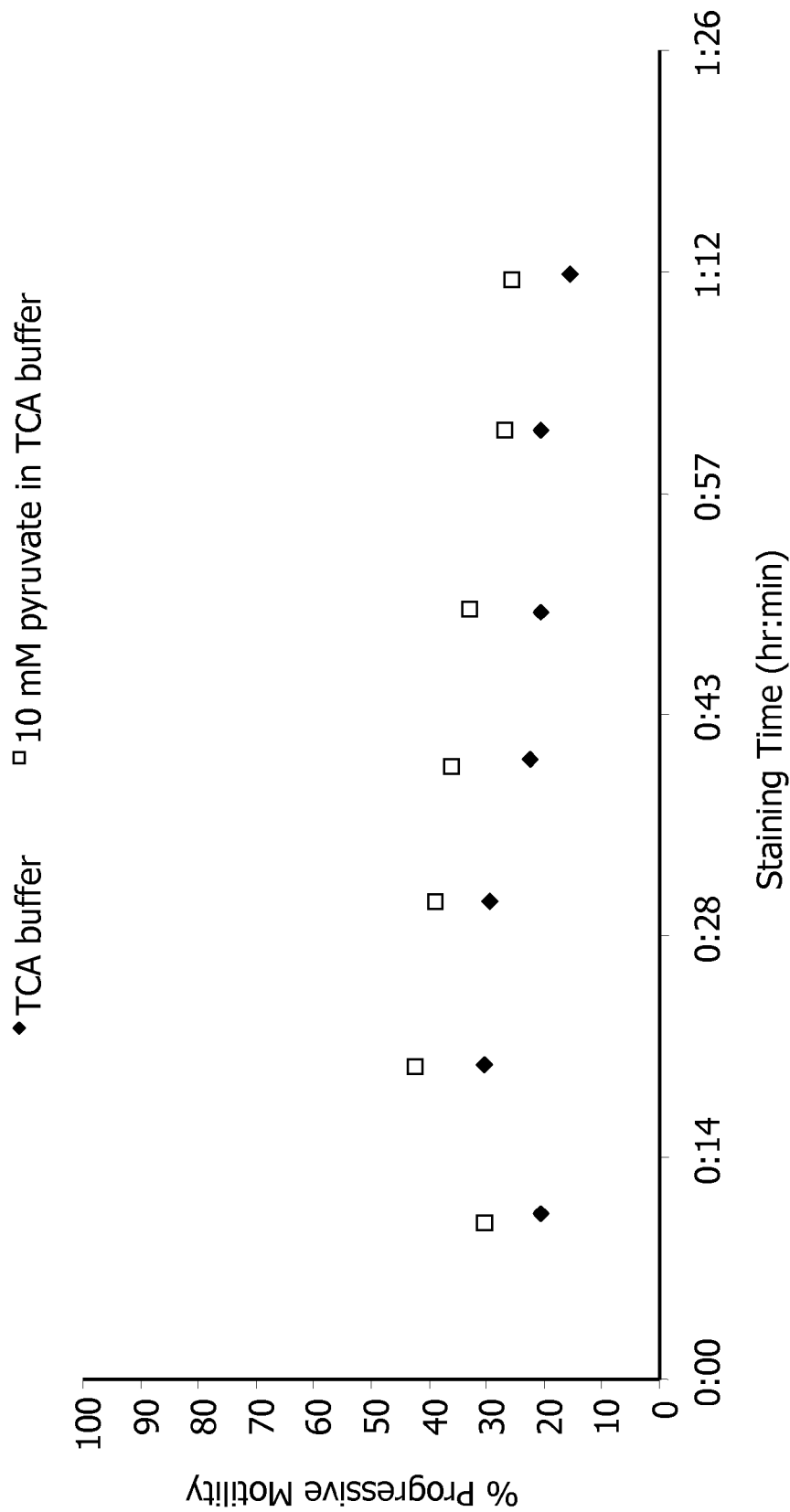
FIG. 14 graphically depicts the results of the study carried out in Example 8 wherein percent progressive motility of sperm is measured for sperm stained with 600 μM Hoechst 33342 dye at 28° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. Theriogenology, 49(4): 871-9 (March 1998)). Based on the semen concentration, 1 mL of $150 \times 10^6$ sperm/ml suspension was prepared by centrifuging the sperm suspension at 500×g for 5 minutes, removing the supernatant and re-suspending the pellet in 28° C. TCA buffer pH 7.3. An additional 1 mL of $150 \times 10^6$ sperm/ml was prepared by suspending an aliquot of semen in 28° C. TCA buffer containing 10 mM pyruvate at pH 7.3. To the sperm suspensions, aliquots of a 10 mM Hoechst solution in water were added to yield the dye concentration of 600 μM Hoechst. The sperm suspensions were maintained in 28° C. water bath for the duration of the staining period. Sperm suspensions were analyzed by removing a 50 μL aliquot from the staining sperm suspension, adding 200 μL of the same buffer at the same temperature and analyzing by IVOS to measure percent progressive motility (% Prog Mot). Results of the IVOS analysis are summarized in FIG. 14.

Example 9

Figure 15:
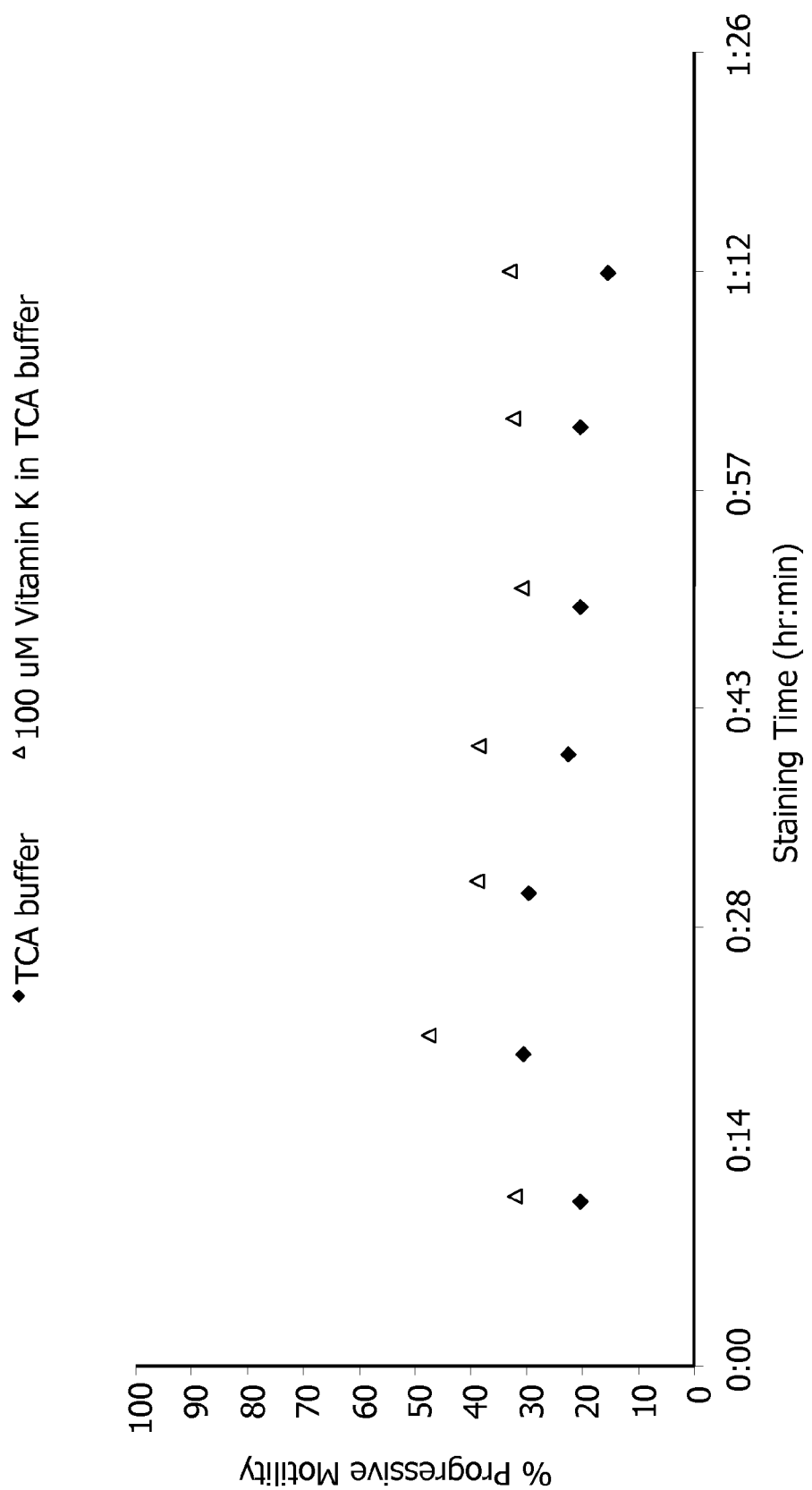
FIG. 15 graphically depicts the results of the study carried out in Example 9 wherein percent progressive motility of sperm is measured for sperm stained with 600 μM Hoechst 33342 dye at 28° C. in either a TCA buffer or a TCA buffer containing 100 μM vitamin K.

Sperm samples were obtained and prepared in the same manner as in Example 8 with the following exception. The buffer used to suspend the sperm for staining and IVOS analysis were TCA and TCA containing 100 uM Vitamin K. Results of the IVOS analysis are summarized in FIG. 15.

Example 10

Figure 16:
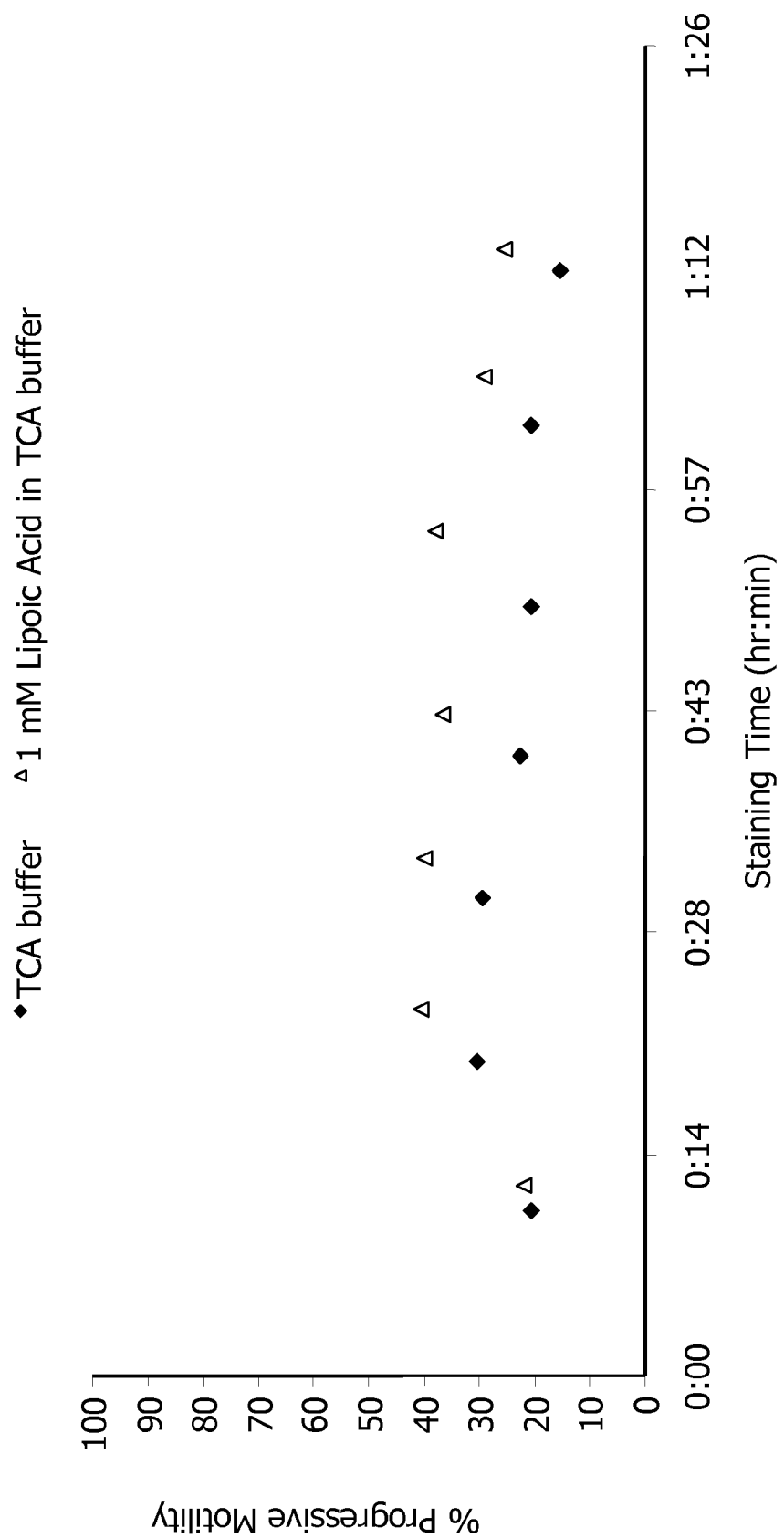
FIG. 16 graphically depicts the results of the study carried out in Example 10 wherein percent progressive motility of sperm is measured for sperm stained with 600 μM Hoechst 33342 dye at 28° C. in either a TCA buffer or a TCA buffer containing 1 mM lipoic acid.

Sperm samples were obtained and prepared in the same manner as in Example 8 with the following exception. The buffer used to suspend the sperm for staining and IVOS analysis were TCA and TCA containing 1 mM Lipoic Acid. Results of the IVOS analysis are summarized in FIG. 16.

Example 11

Figure 17:
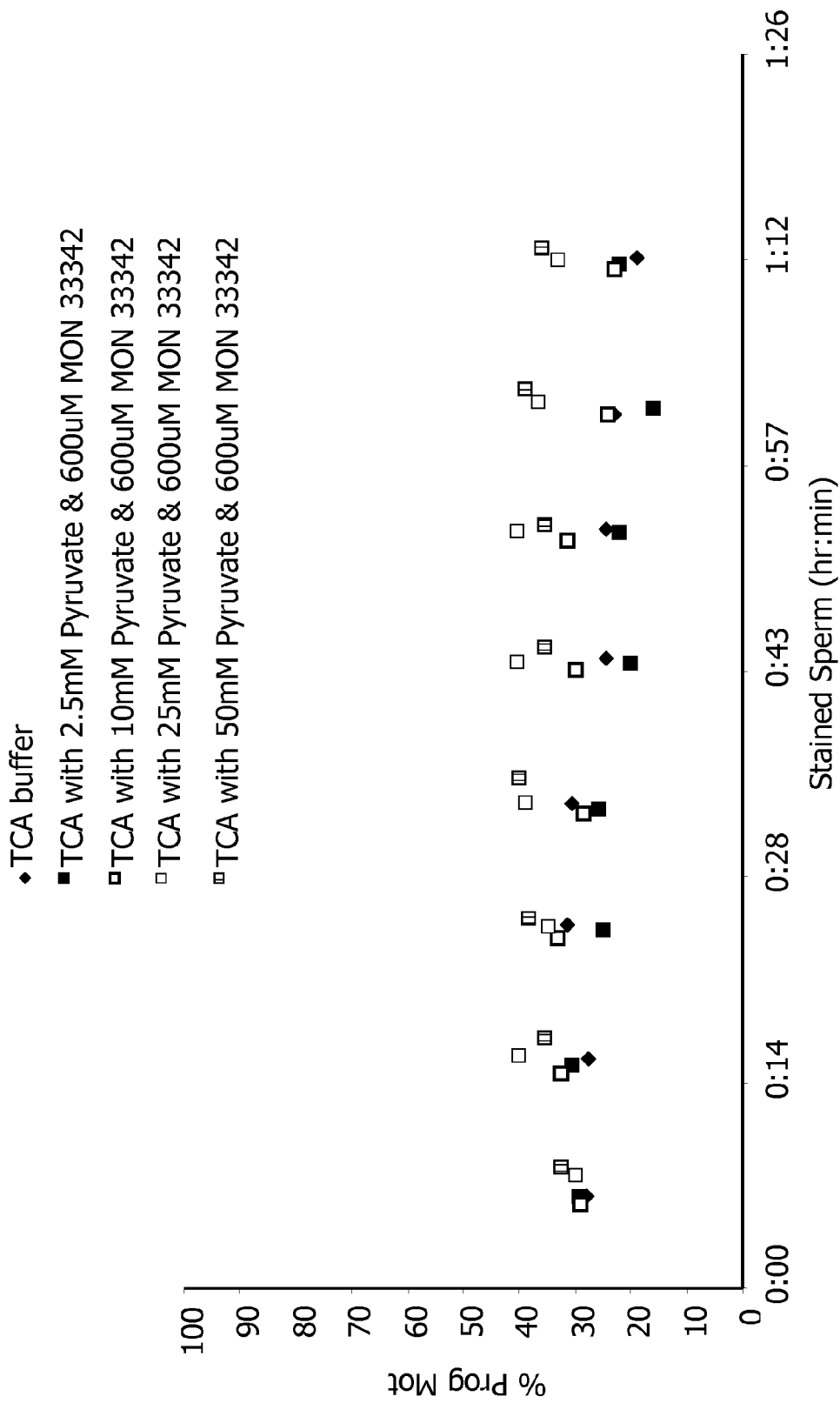
FIG. 17 graphically depicts the results of the study carried out in Example 11 wherein percent progressive motility of sperm is measured for sperm stained with 600 μM Hoechst 33342 dye at 28° C. in a TCA buffer, a TCA buffer containing 2.5 mM pyruvate, a TCA buffer containing 10 mM pyruvate, a TCA buffer containing 25 mM pyruvate, and a TCA buffer containing 50 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology,* 49(4): 871-9 (March 1998)). Based on the semen concentration, 1 mL of $150 \times 10^6$ sperm/ml suspensions were prepared by removing an aliquots of the carbonate sperm suspension, centrifuging the sperm suspension at 500×g for 5 minutes, removing the supernatant and re-suspending the pellet in 1 ml TCA buffer or in 1 ml TCA buffer with 2.5 mM, 10 mM, 25 mM, or 50 mM pyruvate. To the samples was added MON33342 solution to yield the final dye concentrations of 600 μM. The suspensions were incubated in a 28° C. water bath. Stained sperm suspensions were analyzed by removing a 50 μL aliquot from the staining sperm suspension, adding 200 μL of the same buffer at the same temperature and analyzing by IVOS to measure percent progressive motility (% Prog Mot). IVOS results for % Prog Mot are shown in FIG. 17.

Example 12

Figure 18:
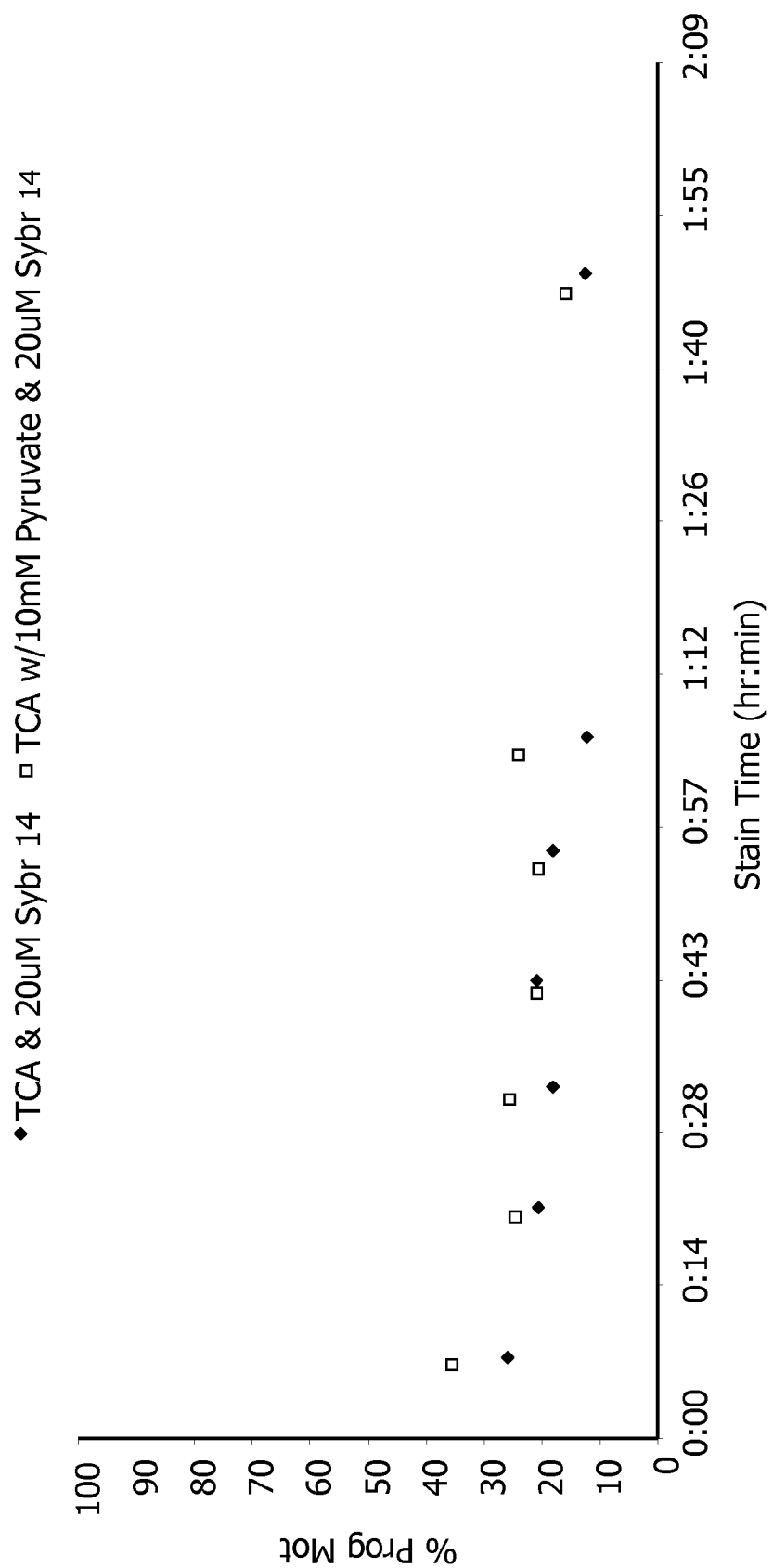
FIG. 18 graphically depicts the results of the study carried out in Example 12 wherein percent progressive motility of sperm is measured for sperm stained with 20 μM SYBR-14 dye at 28° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of $150 \times 10^6$ sperm/ml suspension in TCA buffer was prepared by removing an aliquot of the carbonate sperm suspension, centrifuging the sperm suspension at 500×g for 5 minutes, removing the supernatant and re-suspending the pellet in 1 mL TCA buffer. 1 ml of $150 \times 10^6$ sperm/ml suspension in 10 mM pyruvate in TCA was prepared by removing an aliquot of the carbonate sperm suspension, centrifuging the sperm suspension at 500×g for 5 minutes, removing the supernatant and re-suspending the pellet in 1 mL of 10 mM pyruvate TCA buffer. To samples was added SYBR 14 dye solution to yield the final dye concentrations of 20 µM The suspensions were incubated in a 28° C. water bath. Sperm suspensions were analyzed by removing a 50 µL aliquot from the staining sperm suspension, adding 200 µL of the same buffer at the same temperature and analyzing by IVOS to measure percent progressive motility (% Prog Mot). IVOS results for % Prog Mot are shown in FIG. 18.

Example 13

Figure 19:
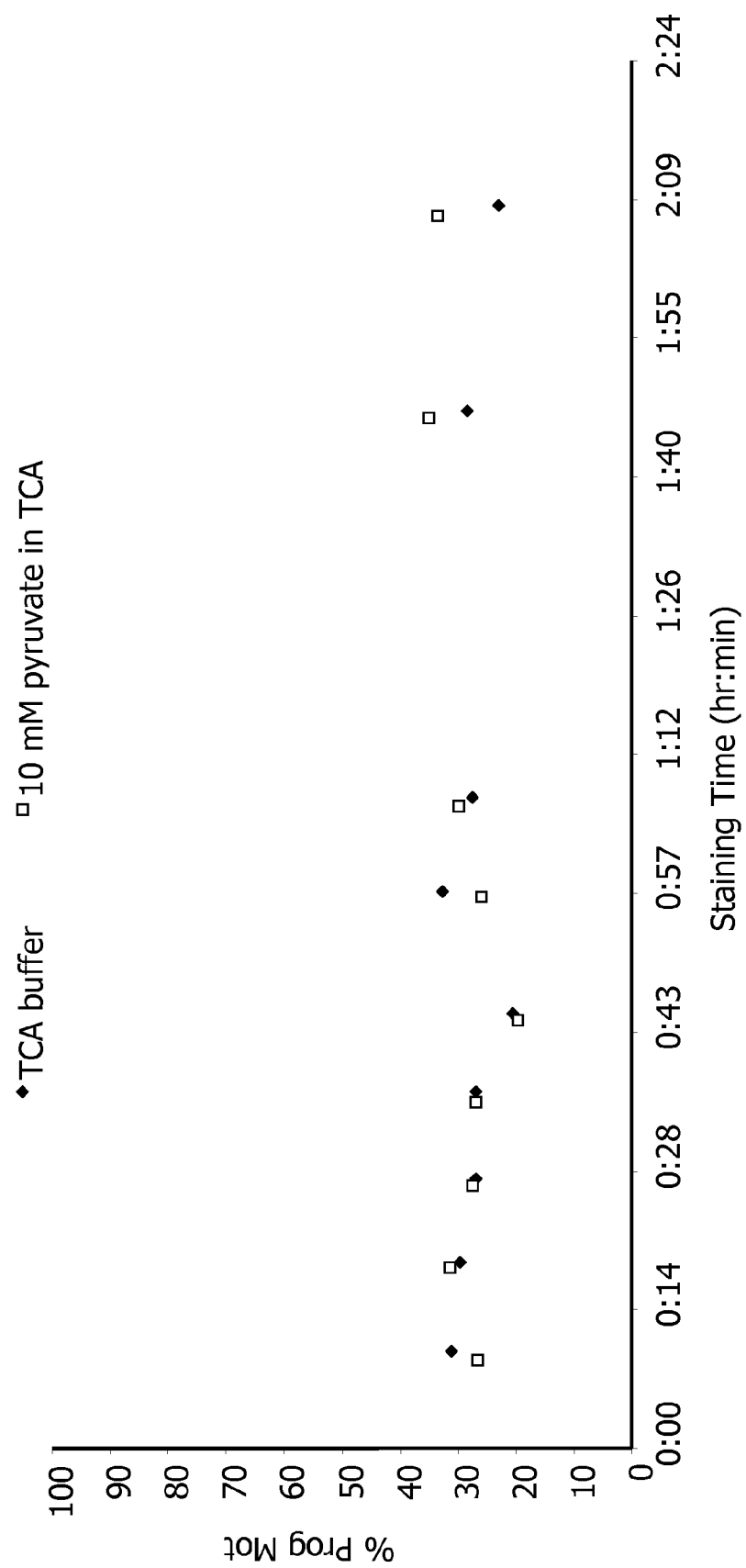
FIG. 19 graphically depicts the results of the study carried out in Example 13 wherein percent progressive motility of sperm is measured for sperm stained with 100 μM BBC dye at 28° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49(4): 871-9 (March 1998)). Based on the semen concentration, 1 mL of $150 \times 10^6$ sperm/ml suspension in TCA buffer was prepared by removing an aliquot of the carbonate sperm suspension, centrifuging the sperm suspension at 500×g for 5 minutes, removing the supernatant and re-suspending the pellet in 1 mL TCA buffer. 1 ml of $150 \times 10^6$ sperm/ml suspension in 10 mM pyruvate in TCA was prepared by removing an aliquot of the carbonate sperm suspension, centrifuging the sperm suspension at 500×g for 5 minutes, removing the supernatant and re-suspending the pellet in 1 ml of 10 mM pyruvate TCA buffer. To the samples was added BBC solution to yield the final dye concentrations of 100 µM. The suspensions were incubated in a 28° C. water bath. Stained sperm suspensions were analyzed by removing a 50 µL aliquot from the staining sperm suspension, adding 200 µL of the same buffer at the same temperature and analyzing by IVOS to measure percent progressive motility (% Prog Mot). IVOS results for % Prog Mot are shown in FIG. 19.

Example 14

Figure 20:
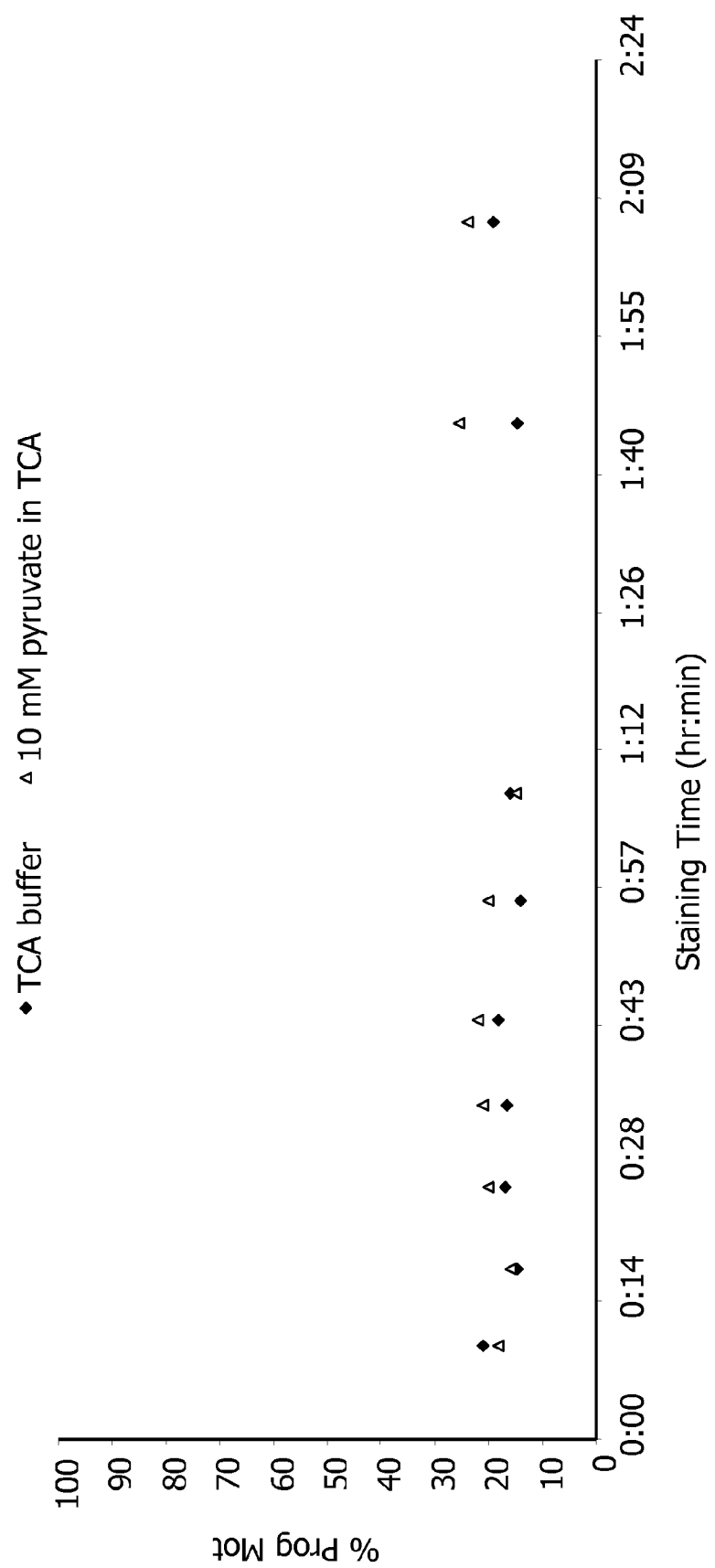
FIG. 20 graphically depicts the results of the study carried out in Example 14 wherein percent progressive motility of sperm is measured for sperm stained with 200 μM BBC dye at 28° C. in either a TCA buffer or a TCA buffer containing 10 mM pyruvate.

Sperm samples were obtained and prepared in the same manner as in Example 4 with the following exception. The staining concentration was 200 uM BBC. Results of the IVOS analysis are summarized in FIG. 20.

What is claimed is:

1. A method of making a gender enriched sperm cell suspension comprising mixing a sperm cell suspension with a composition which inhibits motility to form a chemically immotile sperm cell suspension, staining said chemically immotile sperm cell suspension with a DNA-selective dye and sorting the stained chemically immotile sperm cell suspension to form a viable, gender enriched insemination population of X chromosome bearing or Y chromosome bearing sperm cells having a DNA-selected dye associated with their DNA.

2. The method of claim 1, wherein the dye is selected from the group consisting of Hoechst 33342, Hoechst 33258, SYBR-14, and bisbenzimide-BODIPY® conjugate 6-{[3 ((2Z)-2-{[1-(difluoroboryl)-3,5-dimethyl-1H-pyrrol-2-yl]methylene}-2H-pyrrol-5-yl)propanoyl]amino}-N- [3-(methyl{3[({4- [6-(4-methylpiperazin-1-yl)-1H, 3'H-2,5'-bibenzimidazol-2'-yl]phenoxy}acetyl) amino]propyl} amino)propyl]hexanamide.

3. The method of claim 1, wherein the chemically immotile sperm cell suspension is rendered chemically immotile during the sorting process by a composition which inhibits motility comprising a source of carbonate.

4. The method of claim 3, wherein said chemically immotile sperm cell suspension is rendered chemically immotile during the sorting process by a composition which inhibits motility comprising $NaHCO_3$, $KHCO_3$, and $C_6H_8O_7 \cdot H_2O$.

5. The method of claim 4, wherein said chemically immotile sperm cell suspension is rendered chemically immotile during the sorting process by a composition which inhibits motility comprising 0.097 moles/L of $NaHCO_3$, 0.173 moles/L of $KHCO_3$, 0.090 moles/L $C_6H_8O_7 \cdot H_2O$ in water.

6. The method of claim 1, wherein a concentration of said viable, gender enriched insemination population of X chromosome bearing sperm cells or Y chromosome bearing sperm cells sperm in the suspension is at least $1.25 \times 10^8$ spermatozoa per ml.

7. The method of claim 1, wherein a concentration of said viable, gender enriched insemination population of X chromosome bearing sperm cells or Y chromosome bearing sperm cells sperm in the suspension is at least $1.5 \times 10^8$ spermatozoa per ml.

8. The method of claim 1, wherein a concentration of said viable, gender enriched insemination population of X chromosome bearing sperm cells or Y chromosome bearing sperm cells sperm in the suspension is at least $1.75 \times 10^8$ spermatozoa per ml.

9. The method of claim 1, wherein a concentration of said viable, gender enriched insemination population of X chromosome bearing sperm cells or Y chromosome bearing sperm cells sperm in the suspension is less than about $9.0 \times 10^5$ spermatozoa per ml.

10. The method of claim 1, wherein a concentration of said viable, gender enriched insemination population of X chromosome bearing sperm cells or Y chromosome bearing sperm cells sperm in the suspension is less than about $7 \times 10^5$ spermatozoa per ml.

11. The method of claim 1, wherein a concentration of said viable, gender enriched insemination population of X chromosome bearing sperm cells or Y chromosome bearing sperm cells sperm in the suspension is less than about $5 \times 10^5$ spermatozoa per ml.

12. The method of claim 1, wherein a concentration of said viable, gender enriched insemination population of X chromosome bearing sperm cells or Y chromosome bearing sperm cells sperm in the suspension is less than about $2 \times 10^5$ spermatozoa per ml.

13. The method of claim 1, wherein a concentration of said viable, gender enriched insemination population of X chromosome bearing sperm cells or Y chromosome bearing sperm cells sperm in the suspension is less than about $1 \times 10^5$ spermatozoa per ml.

14. The method of claim 1, wherein said viable spermatozoa suspension comprises viable frozen spermatozoa sperm.

15. The, method of claim 1, wherein a concentration of said viable, gender enriched insemination population of X chromosome bearing sperm cells or Y chromosome bearing sperm cells is sperm in the suspension being less than about $1\times10^6$ or at least about $1\times10^8$ sperm per ml.

16. The method of claim 1, wherein the chemically immotile sperm cell suspension is rendered chemically immotile during the sorting process in a suspension comprising potassium and sodium, wherein the molar ratio of potassium to sodium is greater than 1:1, respectively.

17. The method of claim 16, wherein the molar ratio of potassium to sodium is greater than 1.25:1, respectively.

18. The method of claim 16, wherein the molar ratio of potassium to sodium is greater than 1.5:1, respectively.

19. The method of claim 16, wherein the molar ratio of potassium to sodium is greater than 1.75:1, respectively.

20. The method of claim 16, wherein the molar ratio of potassium to sodium is greater than 2:1, respectively.

* * * * *